United States Patent
Dharmakumar et al.

(10) Patent No.: US 11,129,911 B2
(45) Date of Patent: Sep. 28, 2021

(54) ASSESSMENT OF CORONARY HEART DISEASE WITH CARBON DIOXIDE

(71) Applicant: Cedars-Sinai Medical Center, Los Angeles, CA (US)

(72) Inventors: Rohan Dharmakumar, Moorpark, CA (US); Debiao Li, San Marino, CA (US); Sotirios A. Tsaftaris, Lucca (IT)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 559 days.

(21) Appl. No.: 15/910,718

(22) Filed: Mar. 2, 2018

(65) Prior Publication Data

US 2019/0038781 A1 Feb. 7, 2019

Related U.S. Application Data

(63) Continuation-in-part of application No. 15/672,162, filed on Aug. 8, 2017, which is a continuation of
(Continued)

(51) Int. Cl.
 *A61K 49/08* (2006.01)
 *A61K 31/7076* (2006.01)
 *A61K 33/00* (2006.01)

(52) U.S. Cl.
 CPC .......... *A61K 49/08* (2013.01); *A61K 31/7076* (2013.01); *A61K 33/00* (2013.01); *A61K 2300/00* (2013.01)

(58) Field of Classification Search
 CPC .... A61K 49/08; A61K 31/7076; A61K 33/00; A61K 2300/00
 See application file for complete search history.

(56) References Cited

U.S. PATENT DOCUMENTS

| 5,558,083 A | 9/1996 | Bathe et al. |
| 5,670,177 A | 9/1997 | Briend et al. |

(Continued)

FOREIGN PATENT DOCUMENTS

| AU | 2012250539 A1 | 12/2013 |
| CA | 2845308 A1 | 11/2012 |

(Continued)

OTHER PUBLICATIONS

Eckenhoff, J. E. et al. "The coronary circulation in the dog." American Journal of Physiology-Legacy Content 148.3 (1947): 582-596.

(Continued)

*Primary Examiner* — Sanjay Cattungal

(74) *Attorney, Agent, or Firm* — Nixon Peabody LLP; Linda B. Huber; Suwei Zhu

(57) ABSTRACT

There are provided methods for diagnosing coronary heart disease in a subject in need thereof comprising administering an admixture comprising $CO_2$ to a subject to reach a predetermined $PaCO_2$ in the subject to induce hyperemia, monitoring vascular reactivity in the subject and diagnosing the presence or absence of coronary heart disease in the subject, wherein decreased vascular reactivity in the subject compared to a control subject is indicative of coronary heart disease. There are also provided methods for increasing sensitivity and specificity of BOLD MRI.

20 Claims, 20 Drawing Sheets

Related U.S. Application Data application No. 14/075,918, filed on Nov. 8, 2013, now abandoned, which is a continuation-in-part of application No. 14/115,860, filed as application No. PCT/US2012/036813 on May 7, 2012.

(60) Provisional application No. 61/482,956, filed on May 5, 2011.

(56) References Cited

U.S. PATENT DOCUMENTS

| | | | |
|---|---|---|---|
| 5,975,748 | A | 11/1999 | East, IV et al. |
| 6,001,332 | A | 12/1999 | Garrett |
| 6,013,243 | A | 1/2000 | Achilefu |
| 7,073,501 | B2 | 7/2006 | Remmers et al. |
| 7,941,204 | B1 | 5/2011 | Wang et al. |
| 8,290,226 | B2 | 10/2012 | Gühring et al. |
| 8,936,777 | B2 | 1/2015 | Cesati et al. |
| 2002/0103454 | A1 | 8/2002 | Sackner et al. |
| 2002/0185129 | A1 | 12/2002 | Fisher et al. |
| 2003/0017612 | A1* | 1/2003 | Gerber ............... G01R 33/50 436/173 |
| 2004/0081623 | A1 | 4/2004 | Eriksen et al. |
| 2004/0206354 | A1 | 10/2004 | Fisher et al. |
| 2005/0124907 | A1 | 6/2005 | Kuck et al. |
| 2005/0165311 | A1 | 7/2005 | Porter et al. |
| 2005/0228337 | A1 | 10/2005 | Rasor et al. |
| 2005/0238727 | A1* | 10/2005 | Cagnoni ............. A61K 41/00 424/600 |
| 2006/0239524 | A1 | 10/2006 | Desh et al. |
| 2006/0264755 | A1 | 11/2006 | Maltz et al. |
| 2007/0169779 | A1 | 7/2007 | Freeman |
| 2007/0259966 | A1* | 11/2007 | Cagnoni ............. A61P 35/00 514/716 |
| 2007/0287897 | A1 | 12/2007 | Faris |
| 2007/0299136 | A1* | 12/2007 | Johnson ............... A61P 3/10 514/563 |
| 2008/0058709 | A1 | 3/2008 | Da Silva Freitas |
| 2008/0171933 | A1 | 7/2008 | Li et al. |
| 2010/0086483 | A1 | 4/2010 | Belardinelli et al. |
| 2010/0240983 | A1 | 9/2010 | Jung et al. |
| 2010/0305459 | A1 | 12/2010 | Whitt et al. |
| 2014/0053837 | A1* | 2/2014 | Klein ............... A61M 16/20 128/203.14 |
| 2014/0088406 | A1 | 3/2014 | Dharmakumar et al. |
| 2014/0170069 | A1 | 6/2014 | Dharmakumar et al. |
| 2015/0196207 | A1 | 7/2015 | Friedrich et al. |
| 2016/0045841 | A1* | 2/2016 | Kaplan ............... B01D 3/06 429/49 |
| 2018/0185519 | A1 | 7/2018 | Dharmakumar et al. |

FOREIGN PATENT DOCUMENTS

| | | |
|---|---|---|
| CA | 2832851 A1 | 5/2015 |
| EP | 2704577 A1 | 3/2014 |
| WO | WO-2000057776 | 10/2000 |
| WO | 2000/078774 A1 | 12/2000 |
| WO | 2001/064280 A1 | 9/2001 |
| WO | 2007/084264 A1 | 7/2007 |
| WO | WO-2008122056 | 10/2008 |
| WO | WO-2010033971 | 3/2010 |
| WO | WO-2010141081 | 12/2010 |
| WO | WO-2012151583 | 11/2012 |

OTHER PUBLICATIONS

Feigl, E. O. "Coronary physiology." Physiological reviews 63.1 (1983): 1-205.
Momen, Afsana, et al. "Coronary blood flow responses to physiological stress in humans." Am J Physiol Heart Circ Physiol 296 (2009): H854-H861.
Scheuer J. "The effects of respiratory and metabolic alkalosis on coronary flow, hemodynamics and myocardial carbohydrate metabolism." Cardiology 52.5 (1968): 275-286.
Baddeley, Hi, et al. "Gas exchange parameters in radiotherapy patients during breathing of 2%, 3.5% and 5% carbogen gas mixtures." The British journal of radiology 73.874 (2000): 1100-1104.
U.S. Appl. No. 14/115,860, Assessment of Coronary Heart Disease with Carbon Dioxide, filed Nov. 5, 2013.
U.S. Appl. No. 15/672,162, Assessment of Coronary Heart Disease with Carbon Dioxide, filed Aug. 8, 2017.
Araujo, Luis I., et al. "Noninvasive quantification of regional myocardial blood flow in coronary artery disease with oxygen-15-labeled carbon dioxide inhalation and positron emission tomography." Circulation 83.3 (1991): 875-885.
Back et al., Angiography with Carbon Dioxide ($CO_2$), Surgical Clinics of North America, vol. 76, Issue 4, pp. 575-591, Aug. 1, 1998 [Abstract Only].
Baddeley, Hi, et al. "Gas exchange parameters in radiotherapy patients during breathing of 2%, 3.5% and 5% carbogen gas mixtures." The British journal of radiology 73.874 (2000): 1100-1104. [Abstract Only].
Case, Robert B., et al. "Relative effect of $CO_2$ on canine coronary vascular resistance." Circulation research 42.3 (1978): 410-418.
CIPO, Examination Report, dated Dec. 20, 2018, re Canadian Patent Application No. 2845308.
CIPO. Examination Report, dated Sep. 24, 2019, re Canadian Patent Application No. 2832851.
De Bruyne, Bernard, et al. "Coronary flow reserve calculated from pressure measurements in humans. Validation with positron emission tomography." Circulation 89.3 (1994): 1013-1022.
EPO, Communication pursuant to Article 94(3) EPC, dated Apr. 23, 2019, re European Patent Application No. 16835871.1.
EPO, Communication pursuant to Article 94(3) EPC, dated May 23, 2019, re European Patent Application No. 12779635.7.
EPO. Supplemental European Search Report, dated Apr. 9, 2019, re European Patent Application No. 16845248.0.
EPO, Supplementary European Search Report, dated Jul. 17, 2018, re European Patent Application No. 16835871.1.
Final Office Action on co-pending (U.S. Appl. No. 14/075,918), dated Feb. 8, 2017.
Final Office Action on co-pending (U.S. Appl. No. 14/115,860), dated Nov. 6, 2015.
Foster RS and Blaine J, (1977). 'Urban Tree Survival: Trees in the Sidewalk,' J Arboricult, 4(1):14-7.
International Search Report on corresponding PCT application (PCT/US2012/036813) from International Searching Authority (USPTO) dated Aug. 7, 2012.
IPRP for PCT/US2012/036813, dated Jun. 11, 2013, 15 pages.
Kaufmann, Philipp A., and Paolo G, Carnici. "Myocardial blood flow measurement by PET: technical aspects and clinical applications." Journal of Nuclear Medicine 46.1 (2005): 75-88.
Ledingham, I. McA, et al. "The effect of hypercapnia on myocardial blood flow and metabolism." The Journal of physiology. 210.1 (1970): 87-105.
Non-Final Office Action on co-pending (U.S. Appl. No. 14/075,918), dated May 2, 2016.
Non-Final Office Action on co-pending (U.S. Appl. No. 14/115,860), dated Apr. 10, 2015.
Prisman, Ellan, et el. "Comparison of the effects of independently-controlled end-tidel $PCO_2$ and $PO_2$ on blood oxygen level-dependent (BOLD) MRI." Journal of Magnetic Resonance Imaging: An Official Journal of the International Society for Magnetic Resonance in Medicine 27.1 (2008): 185-191.
Schuster, Andreas, et al. "An isolated perfused pig heart model for the development, validation and translation of novel cardiovascular magnetic resonance techniques." Journal of Cardiovascular Magnetic Resonance 12.1 (2010): 53.
USPTO, Non-Final Rejection, dated Jan. 3, 2020, re U.S. Appl. No. 14/115,860.
Wacker et al., "Changes in Myocardial Oxygenation and Perfusion Under Pharmacological Stress With Dipyridamole: Assessment Using T'2 and T1 Measurements," Magnetic Resonance In Medicine, 41:686-695 (1999).

(56) References Cited

OTHER PUBLICATIONS

Written Opinion on corresponding PCT application (PCT/US2012/036813) from International Searching Authority (USPTO) dated Aug. 7, 2012.
AU 2012250539 Examination Report dated Aug. 4, 2015, 3 pages.
CA 2845308 Office Action dated Oct. 25, 2018, 7 pages.
CA 2832851 A1 Office Action dated Aug. 31, 2020, 6 pages.
EP 12779635.7 Extended European Search Report dated Sep. 17, 2014, 7 pages.
Brandi et al., The Role of Carbon Dioxide Therapy in the Treatment of Chronic Wounds, In Vivo, 2010, vol. 24, pp. 223-226.
Dutton et al., Carbon Dioxide and Liver Blood Flow, Bull. Europ. Physiopath. Resp., 1976, vol. 12, pp. 265-272.
Foex et al., Effects of CO2 on the Systemic and Coronary Circulations and on Coronary Sinus Blood Gas Tensions, Bull. Europ. Physiopath. Resp., 1979, vol. 15, pp. 625-638.
Kashiba et al., From O2 to H2S: A Landscape View of Gas Biology, Kieo J. Med, 2002, vol. 51(1), pp. 1-10.
Kisilevsky et al., Concentration-Dependent Vasoconstrictive Effect of Hyperoxia on Hypercarbia-Dilated Retinal Arterioles, Microvascular Research, 2008, vol. 75, pp. 263-268.
Van den Elshout et al., Effects of Hypercapnia and Hypocapnia on Respiratory Resistence in Normal and Asthmatic Subjects, Thorax, 1991, vol. 46, pp. 28-32.
Wennmalm, A., Effect of Cigarette Smoking on Basal and Carbon Dioxide Stimulated Cerebral Blood Flow in Man, Clinical Physiology, 1982, vol. 2, pp. 529-535.

\* cited by examiner

Statistics

Pair sample T test
2 groups : target CO2=30,40mmHg, CO2=50,60mmHg
Values are normalized by the average value of LCX from each dog
Samples from CO2 Ramp UP and Block gas paradigm
N=18:18

LAD

| Difference: -0.11153 | Mean | SD |
|---|---|---|
| Group1 | 0.71328 | 0.11988 |
| Group2 | 0.8248 | 0.07428 |
| t Statistic | DF | Prob>|t| |
| -3.67942 | 17 | 0.00186 |
| Significantly different | | |

RCA

| Difference: -0.11963 | Mean | SD |
|---|---|---|
| Group1 | 0.79736 | 0.14119 |
| Group2 | 0.91699 | 0.12568 |
| t Statistic | DF | Prob>|t| |
| -4.98087 | 17 | 1.14056E-4 |
| Significantly different | | |

LCX

| Difference: -0.14268 | Mean | SD |
|---|---|---|
| Group1 | 0.92478 | 0.09077 |
| Group2 | 1.06746 | 0.08096 |
| t Statistic | DF | Prob>|t| |
| -5.1445 | 17 | 8.10788E-5 |
| Significantly different | | |

BLOOD

| Difference: -0.16278 | Mean | SD |
|---|---|---|
| Group1 | 2.88576 | 0.25895 |
| Group2 | 3.04854 | 0.29902 |
| t Statistic | DF | Prob>|t| |
| -2.00956 | 17 | 0.06063 |
| Not Significantly different | | |

MUSCLE

| Difference: -0.04141 | Mean | SD |
|---|---|---|
| Group1 | 0.59048 | 0.15746 |
| Group2 | 0.6319 | 0.07306 |
| t Statistic | DF | Prob>|t| |
| -1.42538 | 17 | 0.17215 |
| Not Significantly different | | |

AIR

| Difference: -0.02098 | Mean | SD |
|---|---|---|
| Group1 | 0.21484 | 0.04433 |
| Group2 | 0.23582 | 0.05874 |
| t Statistic | DF | Prob>|t| |
| -1.85231 | 17 | 0.08143 |
| Not Significantly different | | |

- Mean hyperemic response (ramps and blocks) is approximately 16%

Figure 9

- Hyperemic adenosine stress BOLD response ~ 12% vs $CO_2$ response ~ 16%

Human Studies

PaCO₂: 45 mmHg
Signal: 240.8

PaCO₂: 35 mmHg
Signal: 217.4

Hyperemic response of ~ 11% for a PaCO2 change of 10 mmHg (from 35 to 45 mmHg)

Targeted arterial blood gas estimates and hemodynamic parameters

| Group Intact (n=10) | $P_{ET}CO_2$ (mmHg) | $P_{ET}O_2$ (mmHg) | SBP (mmHg) | HR (per min) | RPP (mmHg/min×10³) |
|---|---|---|---|---|---|
| Adenosine | 37.5±2.9 | 119.9±7.0 | 128.6±16.8 | 99.6±34.7* | 12.3±4.9* |
| Hypercapnia | 60.6±1.4* | 121.3±5.8 | 130.2±14.3 | 81.8±16.8 | 10.9±2.4 |
| Rest | 36.9±1.6 | 118.3±5.2 | 121.2±12.1 | 65.4±15.2 | 8.2±2.3 |
| Group Stenosis (n=7) | $PaCO_2$ (mmHg) | $PaO_2$ (mmHg) | SBP (mmHg) | HR (per min) | RPP (mmHg/min×10³) |
| Adenosine | 37.3±2.2 | 128.0±4.9 | 111.6±32.2 | 119.8±26.9* | 14.9±6.1* |
| Hypercapnia | 61.6±1.1* | 124.7±5.6 | 118.1±25.2 | 100.2±22.8 | 12.5±5.7* |
| Rest | 35.9±3.4 | 126.1±4.4 | 118.0±30.5 | 75.4±17.0 | 8.9±2.9 |
| Group Caffeine (n=5) | $PaCO_2$ (mmHg) | $PaO_2$ (mmHg) | SBP (mmHg) | HR (per min) | RPP (mmHg/min×10³) |
| Adenosine | 35.1±0.6 | 123.7±3.0 | 125.8±8.0 | 65.4±29.9 | 6.9±1.7 |
| Hypercapnia | 59.9±2.3* | 128.9±6.8 | 128.3±11.6 | 69.8±10.8 | 9.3±3.6 |
| Rest | 34.5±1.2 | 125±3.6 | 124.0±11.2 | 56.6±23.2 | 7.1±4.0 |

Figure 13

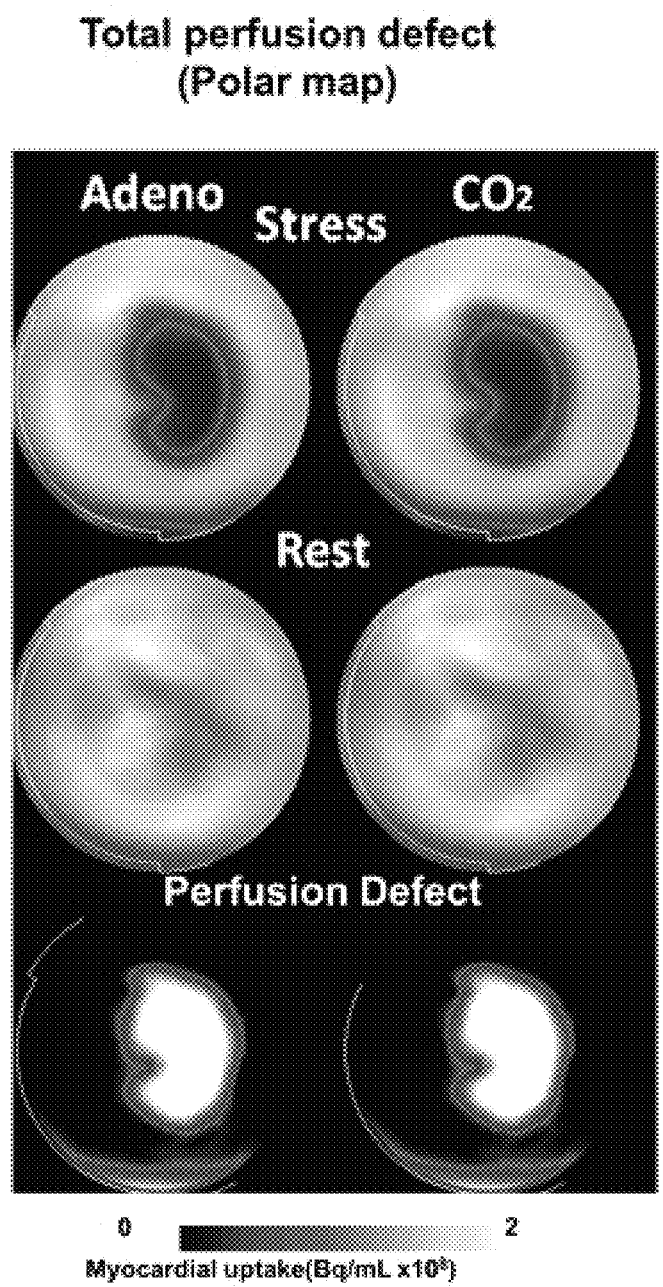
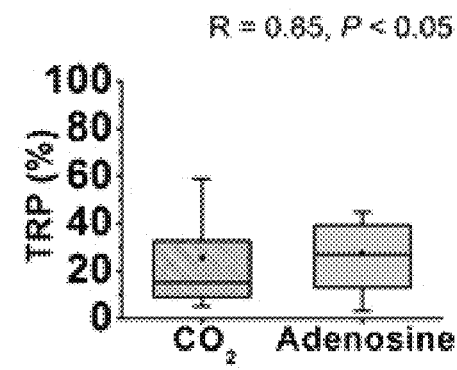
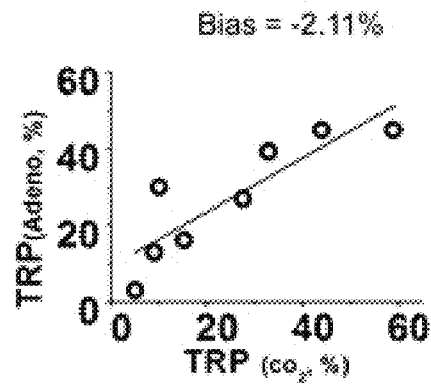
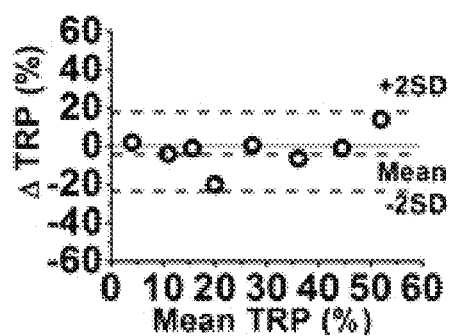
FIG. 17A
FIG. 17B
FIG. 17C
FIG. 17D

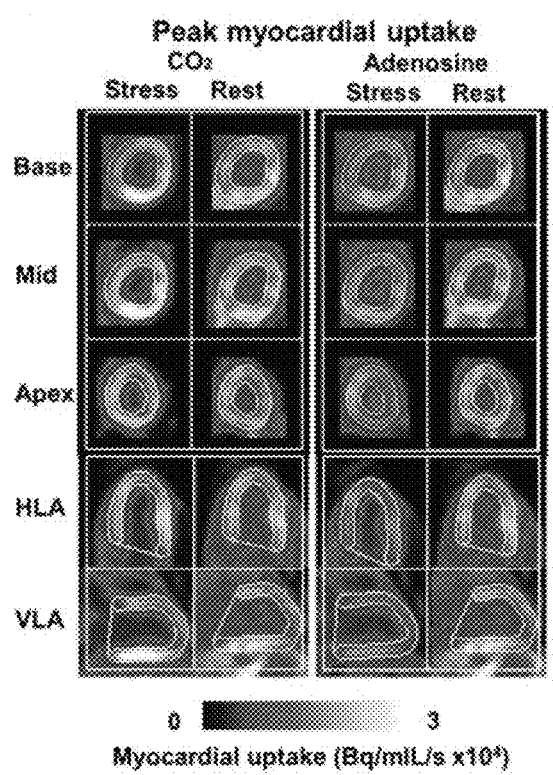
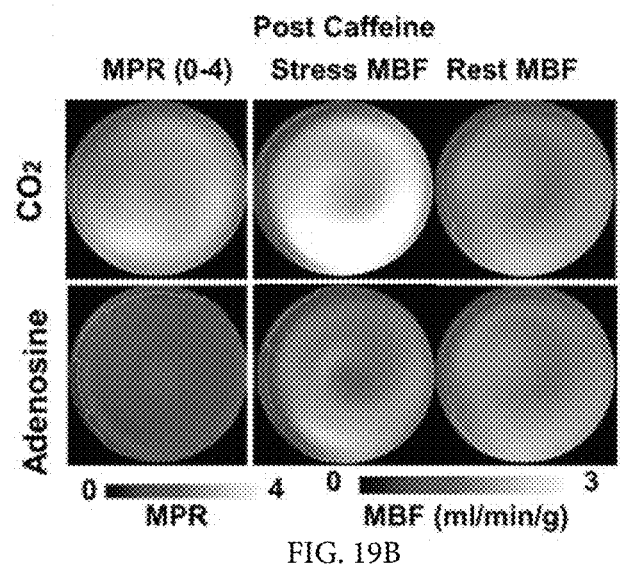
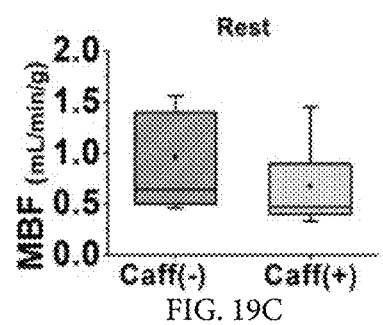
FIG. 19A
FIG. 19B
FIG. 19C

ASSESSMENT OF CORONARY HEART DISEASE WITH CARBON DIOXIDE

CROSS-REFERENCE TO RELATED APPLICATIONS

This application is a Continuation-in-Part of U.S. application Ser. No. 15/672,162 filed on Aug. 8, 2017, which is a Continuation of U.S. application Ser. No. 14/075,918 filed on Nov. 8, 2013, which is a Continuation-in-Part of U.S. application Ser. No. 14/115,860 filed on Nov. 5, 2013, which is a 371 of International Application No. PCT/US2012/036813 filed on May 7, 2012, which claims benefit of priority of U.S. Provisional Application No. 61/482,956 filed on May 5, 2011. The entire contents of each of the aforementioned applications is incorporated herein by reference.

STATEMENT REGARDING FEDERALLY SPONSORED RESEARCH AND DEVELOPMENT

This invention was made with government support under Grant No. HL091989 awarded by the National Institutes of Health. The government has certain rights in the invention.

FIELD

The disclosure is directed to methods for detecting coronary heart disease using carbon dioxide ($CO_2$) to induce hyperemia and monitor vascular reactivity.

BACKGROUND

All publications herein are incorporated by reference to the same extent as if each individual publication or patent application was specifically and individually indicated to be incorporated by reference. The following description includes information that may be useful in understanding the present disclosure. It is not an admission that any of the information provided herein is prior art or relevant to the presently claimed invention, or that any publication specifically or implicitly referenced is prior art. Coronary artery disease (CAD) leads to narrowing of the small blood vessels that supply blood and oxygen to the heart. Typically, atherosclerosis is the cause of CAD. As the coronary arteries narrow, blood flow to the heart can slow down or stop, causing, amongst other symptoms, chest pain (stable angina), shortness of breath and/or myocardial infarction. Numerous tests help diagnose CAD. Such tests include coronary angiography/arteriography, CT angiography, echocardiogram, electrocardiogram (ECG), electron-beam computed tomography (EBCT), magnetic resonance angiography, nuclear scan and exercise stress test. Functional assessment of the myocardium (for example the assessment of myocardium's oxygen status) requires that a patient's heart is stressed either via controlled exercise or pharmacologically.

Assessment of vascular reactivity in the heart is the hallmark of stress testing in cardiac imaging aimed at understanding ischemic heart disease. This is routinely done in Nuclear Medicine with radionuclide injection (such as Thallium) in conjunction with exercise to identify territories of the heart muscle that are subtended by a suspected narrowed coronary artery. In patients who are contraindicated for exercise stress-testing, this approach is typically used in conjunction with hyperemia inducing drugs, for example via adenosine infusion. Reduced coronary narrowing is expected to reduce hyperemic response and the perfusion reserve. Since nuclear methods are hampered by the need for radioactive tracers combined with limited imaging resolution, other imaging methods, such as ultrasound (using adenosine along with microbubble contrast) and MRI (also using adenosine and various conjugates of gadolinium (Gd) (first-pass perfusion) or alterations in oxygen saturation in response to hyperemia, also known as the Blood-Oxygen-Level-Dependent (BOLD) effect) are under clinical investigation. Nonetheless, in patients who are contraindicated for exercise stress-testing, currently all imaging approaches require adenosine to elicit hyperemia. However, adenosine has undesirable side effects (such as the feeling of "impending doom", bradycardia, arrhythmia, transient or prolonged episode of asystole, ventricular fibrillation (rarely), chest pain, headache, dyspnea, and nausea), making it less than favorable for initial or follow-up studies and many patients request that they do not undergo repeated adenosine stress testing. Nonetheless repeated stress testing is indicated in a significant patient population to assess the effectiveness of interventional or medical therapeutic regimens. In view of the side effects of hyperemia inducing drugs, there is a need for alternatives, which induce hyperemia in patients who are contraindicated for exercise stress-testing but do not cause the side effects caused by the existing hyperemia inducing drugs.

SUMMARY

There is provided herein the use of carbon dioxide to replace hyperemia-inducing drugs such as adenosine to induce hyperemia in subjects contra-indicated for exercise stress testing, so as to diagnose coronary heart diseases without the undesirable side effects of drugs such as adenosine. In an embodiment, the $CO_2$ levels are altered while the $O_2$ levels are held constant. In another embodiment, the $CO_2$ levels are controlled by administering a blend of air and a controlled amount of a gas mixture comprising 20% oxygen and 80% carbon dioxide.

In an aspect, there are provided methods for diagnosing coronary heart disease in a subject in need thereof comprising administering an admixture comprising $CO_2$ to a subject to produce a hyperemic response corresponding to at least one selected increase in a subject's coronary $PaCO_2$, monitoring vascular reactivity in the subject and diagnosing the presence or absence of coronary heart disease in the subject. The presence of coronary disease can be detected by monitoring a parameter indicative of a disease-associated change in a vasoreactive response to the at least one increase in $PaCO_2$ in at least one coronary blood vessel or region of the heart. The present technology is based, at least in part, on the finding that such a change can be captured by monitoring the quantum of change in a parameter affected by a change in $PaCO_2$, from an first $PaCO_2$ level to a second $PaCO_2$ level, for example a parameter correlated with vasodilation such as increased blood flow.

An observation of a change in a vasodilatory response can be extended to comparing responses among different subjects, wherein a decreased vascular reactivity in a subject in need of a diagnosis compared to that of a control subject is indicative of coronary heart disease.

Thus, according to one embodiment, there is provided a method for assessing hyperemic response in a subject in need thereof comprising administering an admixture comprising $CO_2$ to a subject to reach a predetermined $PaCO_2$ in the subject to induce hyperemia, monitoring vascular reactivity in the subject and assessing hyperemic response in the subject, wherein decreased vascular reactivity in the subject compared to a control subject is indicative of poor hyperemic response, thereby assessing hyperemic response in the subject in need thereof.

In some embodiments, methods provided herein are directed to assessing organ perfusion in a subject in need thereof.

In some embodiments, methods provided herein are directed to assessing vascular reactivity of an organ in a subject in need thereof.

In another aspect, there are provided methods of producing coronary vasodilation in a subject in need thereof comprising administering an admixture comprising $CO_2$ to a subject to reach a predetermined $PaCO_2$ in the subject so as to produce coronary vasodilation, thereby producing coronary vasodilation in the subject.

In yet another aspect, there are provided methods for increasing sensitivity and specificity for BOLD MRI. The method includes administering an admixture comprising $CO_2$ to a subject to reach a predetermined $PaCO_2$ in the subject to induce hyperemia and imaging the myocardium using MRI to assess a hypermic response in response to a predetermined modulation in $PaCO_2$. In some embodiments, imaging the myocardium comprises (i) obtaining free-breathing cardiac phase resolved 3D myocardial BOLD images; (ii) registering and segmenting the images to obtain the myocardial dynamic volume; and (iii) identifying ischemic territory and quantifying image volume.

In a further aspect, there is provided the use of a $CO_2$ containing gas for inducing hyperemia in a subject in need of a diagnostic assessment of coronary heart disease, wherein the $CO_2$ containing gas is used to attain at least one increase in a subject's coronary $PaCO_2$ sufficient for diagnosing coronary heart disease from imaging data, wherein the imaging data is indicative of a cardiovascular-disease-associated vasoreactive response to the least one increase in $PaCO_2$ in at least one coronary blood vessel or region of the heart.

In another aspect, there is provided a method for inducing hyperemia in a subject in need of a diagnostic assessment of coronary heart disease comprising administering a $CO_2$ containing gas, attaining at least one increase in a subject's coronary $PaCO_2$ sufficient for diagnosing coronary heart disease from imaging data and imaging the heart during a period in which the increase in $PaCO_2$ is measurable, wherein the imaging data is indicative of a cardiovascular disease-associated vasoreactive response in at least one coronary blood vessel or region of the heart.

In some embodiments, the at least one increase in the subject's $PaCO_2$ is selected to produce a coronary vasoreactive response sufficient for replacing a hyperemia inducing drug in assessing coronary disease. In one embodiment, the hyperemia inducing drug that is replaced is adenosine.

In some embodiments, the methods provided herein comprise attaining a particular predetermined $PaCO_2$.

In some embodiments, the pre-determined $PaCO_2$ is patient specific, i.e. determined relative to a baseline steady level in the patient (also referred to herein as a reference steady state). For example, the pre-determined $PaCO_2$ may be an 8 to 20 mm Hg increase relative to a baseline steady level measured at the time of testing in the patient. In an embodiment, the pre-determined $PaCO_2$ is an increase of about 25 mm Hg relative to a baseline steady level measured at the time of testing in the patient. In some embodiments, the pre-determined $PaCO_2$ is an increase of about 22 mm Hg to about 28 mm Hg, about 22 mm Hg, about 23 mm Hg, about 24 mm Hg, about 25 mm Hg, about 26 mm Hg, about 27 mm Hg, or about 28 mm Hg relative to a baseline steady level measured at the time of testing in the patient.

In some embodiments, the methods provided herein comprise administering carbon dioxide in a stepwise manner.

In some embodiments, the methods provided herein comprise administering carbon dioxide in a block manner.

In some embodiments, the $CO_2$ is administered via inhalation.

In some embodiments, the disease-associated coronary vasoreactive response is assessed relative to a control subject.

In some embodiments, the $PaCO_2$ is increased and decreased repeatedly in the subject.

In some embodiments, the at least one $PaCO_2$ produces at least an 8%-12% increase in a BOLD signal intensity.

In some embodiments, the disease-associated vasoreactive response is a compromised increase in blood flow.

In some embodiments, the imaging data is indicative of the presence or absence of a two-fold increase in blood flow in a coronary artery.

In some embodiments the imaging data are obtained by MRI and the imaging method obtains input of a change in signal intensity of a BOLD MRI signal.

In some embodiments, the imaging method is PET or SPECT and the measure of a disease-associated vasoreactive response is the presence or absence of a threshold increase in blood flow.

In some embodiments, the at least one increase in $PaCO_2$ produces at least a 10% increase in intensity of a BOLD MRI signal.

In some embodiments, the at least one increase in $PaCO_2$ produces a 10-20% increase in intensity of a BOLD MRI signal.

In some embodiments, the methods provided herein comprise: (i) imaging the myocardium to obtain free-breathing cardiac phase resolved 3D myocardial BOLD images; (ii) registering and segmenting the images to obtain the myocardial dynamic volume; and (iii) identifying ischemic territory and quantifing image volume.

In some embodiments, the at least one $PaCO_2$ is at least a 10 mm Hg increase from a first level which is determined to be between 30 and 55 mm Hg. Optionally, the first level is first determined to be between 35 and 45 mm Hg. In some embodiments, the at least one $PaCO_2$ is about a 25 mm Hg increase from a first level which is determined to be between about 20 and about 55 mm Hg. In some embodiments, the at least one $PaCO_2$ is about a 22 mm Hg to about 28 mm Hg, about a 22 mm Hg, about a 23 mm Hg, about a 24 mm Hg, about a 25 mm Hg, about a 26 mm Hg, about a 27 mm Hg, or about a 28 mm Hg increase from a first level which is determined to be between about 20 and about 55 mm Hg, e.g., about 20, about 30, about 35, about 40, about 45, about 50, or about 55 mm Hg. In one embodiment, the at least one PaCO2 is about a 25 mm Hg increase from a first level which is determined to be about 35 mm Hg.

In some embodiments, the sufficiency of the increase in $PaCO_2$ is determined by increasing $PaCO_2$ in a stepwise manner.

In some embodiments, the vasoreactive response is sufficient for obtaining a disease-associated change in BOLD MRI signal obtained by administering $CO_2$ in a manner effective to alternate between two or more $PaCO_2$ levels over a period of time and using repeated BOLD MRI measurements to statistically assess the hyperemic response.

In some embodiments, the coronary vasoreactive response corresponds to a vasodilatory response produced by administering a hyperemia inducing drug for a duration and in amount per unit of time effective to assess coronary disease.

In some embodiments, the hyperemia inducing drug is adenosine, wherein adenosine is administered in a regimen of 140 milligrams/litre per minute over 4 to 6 minutes.

In some embodiments, the methods provided herein comprise admixing air with a selected amount of a $CO_2$ containing gas controlled to obtain a predetermined size increase in $PaCO_2$ from a previous value, for example a measured baseline value.

The $CO_2$ containing gas may contain, for example, 75 to 100% $CO_2$. In some embodiments the $CO_2$ containing gas comprises a percentage composition of oxygen in the 18-23% range, optionally about 20%.

In another aspect, there is provided a method for diagnosing coronary heart disease in a subject in need thereof comprising:
  (i) administering an admixture comprising $CO_2$ to a subject in a stepwise or block manner to reach a predetermined $PaCO_2$ in the subject to induce hyperemia;
  (ii) monitoring vascular reactivity in the subject; and
  (iii) diagnosing the presence or absence of coronary heart disease in the subject, wherein decreased vascular reactivity in the subject compared to a control subject is indicative of coronary heart disease,
thereby diagnosing coronary heart disease in the subject in need thereof.

As elaborated below, administering carbon dioxide to alter $PaCO_2$ in block manner, is optionally repeated over time. Optionally carbon dioxide is administered so as to alternate between two or more levels of $PaCO_2$ over a period of time.

Vascular reactivity may be monitored using any one or more of a variety of advanced imaging methods including without limitation positron emission tomography (PET), single photon emission computed tomography/computed tomography (SPECT), computed tomography (CT), and magnetic resonance imaging (MRI), and the like. In some embodiments, vascular reactivity may be measured using FFR.

In one embodiment, an admixture of $CO_2$ and $O_2$ for inducing hyperemia is an admixture in which $O_2$ is present in the range of 19-22%, for example about 20%. Such an admixture can be used, for example, for blending a $CO_2$ containing gas with air for inhalation In this embodiment, $CO_2$ may make up the rest of the admixture (81-78% respectively) or there may be a third gas in the admixture.

In a further aspect, there are provided methods for delivering controlled amounts of carbon dioxide for inspiration by a subject during free breathing in a cardiac imaging procedure, so as to attain at least one altered level of carbon dioxide in the subject's arterial blood, the at least one altered level of carbon dioxide selected to induce a selected hyperemic response in the subject's myocardium over a time period selected for imaging the hyperemic response, the hyperemic response predetermined to enable at least one segment of the subject's myocardium with a relatively reduced hyperemic response to be identified in the cardiac imaging procedure.

In some embodiments, the methods comprise use of a gas flow controller configured to deliver controlled amounts of carbon dioxide for inspiration by the subject during free breathing in a cardiac imaging procedure, so as to attain the desired at least one altered level of carbon dioxide in the subject's arterial blood.

In some embodiments, the methods comprise use of a gas flow controller configured to deliver controlled amounts of carbon dioxide for inspiration by the subject during free breathing in a cardiac imaging procedure, so as to attain the selected hyperemic response in the subject's myocardium. The selected hyperemic response may be, for example, a two-fold increase in the subject's myocardial blood flow relative to a measured baseline value in the subject, or a hyperemic response substantially the same as that obtained using a hyperemia-inducing drug such as adenosine (a reference standard hyperemic response), as described further herein.

In some embodiments, there are provided methods of controlling a gas flow controller wherein the gas flow controller is configured to deliver controlled amounts of carbon dioxide for inspiration by a subject during free breathing in a cardiac imaging procedure, so as to attain the selected at least one altered level of carbon dioxide in the subject's arterial blood and/or the selected hyperemic response in the subject's myocardium.

In one embodiment, the disclosure is directed to a method for measuring a reduced hyperemic response in an ischemic territory of a subject's myocardium during a cardiac imaging procedure, comprising delivering controlled amounts of carbon dioxide for inspiration by a subject during free breathing so as to attain the selected at least one altered level of carbon dioxide in the subject's arterial blood.

In one embodiment, the levels of oxygen in the subject's arterial blood are maintained constant or substantially constant during the imaging procedure.

In one embodiment, normoxia (i.e., normal levels of oxygen) is maintained during the imaging procedure.

In one embodiment, the gas flow controller is configured to attain at least one target end tidal partial pressure ($PETCO_2$) of carbon dioxide that corresponds to the selected at least one altered level of carbon dioxide.

In one embodiment, the gas flow controller is configured to independently attain a target end tidal partial pressure of oxygen that is constant, for example, at a baseline level for the subject at rest.

In one embodiment, the gas flow controller is configured to attain at least one increase in the subject's coronary $PaCO_2$ sufficient for cardiac imaging, cardiac stress testing, diagnosing coronary heart disease from imaging data, etc.

In one embodiment, the gas flow controller is configured to attain the selected at least one altered level of carbon dioxide in a block manner.

In one embodiment, the reduced hyperemic response is less than the selected hyperemic response, wherein the difference between the reduced hyperemic response and the selected hyperemic response is statistically significant.

In one embodiment, the selected hyperemic response is an increase in the subject's myocardial blood flow that is substantially the same as that attained by administering a controlled amount of a hyperemia-inducing drug, e.g., adenosine, over a pre-determined time period.

As used herein, two values are "substantially the same" if they are essentially the same within the error of measurement, if there is no statistically significant difference between them, or if the difference between them is not "functionally significant", i.e., does not affect outcome in the methods provided herein. "Statistically significant" generally means that the difference between two values has a p-value of <0.05, i.e., has a 95% chance of representing a meaningful difference between the two values.

In some embodiments, the selected hyperemic response is characterized with reference to the manifestation of a stress perfusion defect in a subject with ischemic heart disease. For example, in some embodiments, the selected hyperemic response represents a myocardial stress perfusion defect in segments of the heart that are substantially the same as those produced by a controlled amount of a hyperemia-inducing drug such as adenosine. In some embodiments, the selected hyperemic response represents a total stress perfusion defect that is substantially the same (e.g., statistically indistinguishable and/or functionally indistinguishable in the methods described herein) from that produced by a controlled amount of a hyperemia-inducing drug such as adenosine. For example, the total reduction in myocardial perfusion volume as a fraction of total LV volume (TRP, % LV) is substantially the same as that produced by the hyperemia-inducing drug. In some embodiments, when visual scoring of a stress perfusion defect is evaluated, the concordance between the total myocardial segments identified as true positives and true negatives for presence of the perfusion defect are substantially the same as that determined using a hyperemia-inducing drug such as adenosine. The hyperemic response induced in a subject by a controlled amount (e.g., a clinical amount) of a hyperemia-inducing drug such as adenosine is also referred to herein as a "reference standard hyperemic response".

In one embodiment, the hyperemia inducing drug is adenosine or an analog thereof. However, the hyperemia inducing drug is not meant to be limited and other hyperemia inducing drugs may be used in methods provided herein.

In one embodiment, the selected hyperemic response is a two-fold increase in the subject's myocardial blood flow relative to a measured baseline value in the subject.

In one embodiment, the selected hyperemic response is induced by attaining a carbon dioxide level of about 60 to about 65 mm of Hg for at least about one to two minutes in the subject.

In one embodiment, the at least one altered level of carbon dioxide is a 25 mm of Hg increase from a baseline level of carbon dioxide in the subject. A "baseline level" of mmHg in the subject is the level in the subject before beginning the procedure, i.e., before the delivery of carbon dioxide in accordance with the methods described herein. For example, the baseline level may be the level in the subject at rest (normocapnic level); the level in the subject when the subject is breathing at a regulated elevated minute volume (hypocapnic level); or any predetermined or selected starting level for the subject before initiating delivery of carbon dioxide. In some embodiments, for example, the baseline level may be lower than the level in the subject at rest (normal rest levels vary but are typically about 35 to about 45 mm Hg). For example, if the subject's ventilation (minute volume) is regulated to be faster than at rest, then the measured baseline level may be lower than normal rest level for the subject (a hypocapnic level). In one embodiment, the baseline level is about 30 mm Hg for a subject whose $PCO_2$ at rest is about 40 mm Hg. In one embodiment, the baseline level is the normocapnic level for the subject. In another embodiment, the baseline level is the hypnocapnic level for the subject. In some embodiments, the baseline level is about 30 mm of Hg. In some embodiments, the baseline level is about 30 mm of Hg. It should be understood that the baseline level is not meant to be particularly limited and will be selected by the skilled artisan.

In some embodiments, the at least one altered level of carbon dioxide is selected to provide a hyperemic response which is a two-fold increase in the subject's myocardial blood flow relative to a measured baseline value in the subject. In some embodiments, the at least one altered level of carbon dioxide is selected to provide a hyperemic response which is substantially the same as that obtained using a hyperemia-inducing drug such as adenosine. In such embodiments, any altered level of carbon dioxide that provides the desired hyperemic response may be selected.

In some embodiments, the at least one altered level of carbon dioxide is maintained stably in the patient for a time sufficient to induce and enable measurement of a level-related hyperemic response as described herein, e.g., for a predetermined time.

In one embodiment, the cardiac imaging procedure is PET, optionally $^{13}N$ ammonia PET. However, the cardiac imaging procedure is not meant to be particularly limited. Any suitable imaging procedure known in the art may be used with methods described herein.

The at least one altered level of carbon dioxide is generally a level that is maintained within a predetermined confined range so as to induce and enable measurement of a level-related hyperemic response. In this manner, a dose-related response can be measured in a manner comparable to use of a hyperemia inducing drug. For example, a range of 1 to 3 mm of Hg can be maintained using known control algorithms for attaining target end tidal concentrations of carbon dioxide, for example, on a breath by breath basis. In some embodiments, the at least one altered level of carbon dioxide is selected to provide a hyperemic response which is substantially the same as the hyperemic response obtained by a hyperemia inducing drug such as adenosine (e.g., by a standard dose of adenosine). In some embodiments, the at least one altered level of carbon dioxide is selected to provide a hyperemic response which is a two-fold increase in the subject's myocardial blood flow relative to a measured baseline value in the subject. In some embodiments, the at least one altered level of carbon dioxide is selected to provide a hyperemic response which is an increase in the subject's myocardial blood flow relative to a measured baseline value in the subject, which may be substantially the same amount of increase in the subject's myocardial blood flow as is obtained by a hyperemia inducing drug such as adenosine, e.g., a two-fold or more than two-fold increase in myocardial blood flow. In this context, the measured baseline value in the subject is the myocardial blood flow measured in the subject before beginning the procedure, i.e., before the delivery of carbon dioxide in accordance with the methods described herein.

In some embodiments, there are provided methods for cardiac imaging, cardiac stress testing, and the like in accordance with standard procedures known in the art, wherein the use of a hyperemia inducing drug in such procedures is replaced by delivery of controlled amounts of carbon dioxide for inspiration by a subject during free breathing, such that at least one altered level of carbon dioxide in the subject's arterial blood is attained and/or at least a selected hyperemic response in the subject's myocardial blood flow is induced. In some such embodiments, the at least one altered level of carbon dioxide and/or the selected hyperemic response is substantially the same as that obtained by use of the hyperemia inducing drug which is replaced by delivery of $CO_2$ in the procedure. In some such embodiments, there are provided methods for cardiac imaging, cardiac stress testing, measuring a hyperemic response, and the like in subjects in need thereof who have consumed caffeine or a caffeine-containing substance (e.g., chocolate, tea, coffee, etc.) prior to initiating the procedures described herein. Notably, unlike $CO_2$ some hyperemia-inducing drugs do not produce reliable assessments in subjects who have consumed caffeine beforehand.

Methods and systems for controlling a gas delivery device during a cardiac imaging procedure and/or for measuring a hyperemic response are also provided herein.

BRIEF DESCRIPTION OF THE DRAWINGS

For a better understanding of the present invention, as well as other aspects and further features thereof, reference is made to the following description which is to be used in conjunction with the accompanying drawings, where:

FIG. 9 is a table summarizing the statistical BOLD data associated with the $PaCO_2$ modulation in myocardial territories, blood, muscle and air, while $PaO_2$ is held constant.

FIG. 13 is a table summarizing estimates of mean arterial CO2, O2, and hemodynamic variables of interest in group stenosis. SBP: Systolic Arterial Blood Pressure; HR: Heart Rate; RPP: Rate Pressure Product (MAP×HR). * denotes P<0.05 in comparison to rest values.

FIG. 14A and FIG. 14B show the corresponding dynamic radiotracer uptake curves, which show the increased myocardial uptake responses to hypercapnia and adenosine stresses relative to rest. FIG. 14C and FIG. 14D show the global mean MBF and the corresponding MPR at rest and under hypercapnia and adenosine. * denotes P<0.05.

FIG. 15A shows representative short and long-axis PET images of peak myocardial uptake of $^{13}$N-ammonia during hypercapnia of $PaCO_2$~60 mmHg ($CO_2$), standard clinical dose of adenosine (Adenosine) and at rest with $PaCO_2$~35 mmHg (Rest) in a canine with a LAD stenosis. Note the lower uptake of the radiotracer in the anterior lateral wall (lower signal in distal LAD segments, yellow arrows) under hypercapnia and adenosine. For the case in FIG. 15A, rest and stress MBF (under hypercapnia and adenosine) and corresponding MPR are shown as polar maps in FIG. 15B. These images show marked reduction in MBF and MPR in the LAD territory, which are visually evident and spatially concordant under hypercapnia and adenosine.

FIG. 16A, FIG. 16B and FIG. 16E show mean regional MBF at rest, hypercapnia and adenosine. Regional MBF under hypercapnia and adenosine showed good correlation and agreement. FIG. 16C, FIG. 16D and FIG. 16F show corresponding MPR under hypercapnia and adenosine with similar results. * denotes P<0.05 compared to conditions of rest; and + denotes P<0.05 compared to LAD under stress.

FIGS. 17A-17D depict depicts total myocardial perfusion defect due to coronary stenosis under hypercapnia and adenosine. FIG. 17A shows the perfusion defects detected from the Change Analysis estimated from time-averaged myocardial uptake images at rest and stress (hypercapnia and adenosine), the polar images highlighting total perfusion defects (right). Note the near identical correspondence in the perfusion defect territories identified in the slices and the whole heart under hypercapnia and adenosine. FIG. 17B shows the mean TRP (% LV) under hypercapnia and adenosine. No significant difference in TRP (% LV) was observed under hypercapnia and adenosine. FIG. 17C and FIG. 17D show results from linear regression and Bland-Altman analyses.

FIGS. 19A-19C depict global and regional myocardial blood flow response to hypercapnia and adenosine following caffeine administration. FIG. 19A shows representative short- and long-axis PET images acquired during peak myocardial uptake of $^{13}$N-ammonia under hypercapnia of $PaCO_2$~60 mmHg ($CO_2$), standard adenosine dose (Adenosine) and at baseline conditions with $PaCO_2$~35 mmHg (Rest) post caffeine administration. These visual results show that the increase in myocardial uptake of radiotracer relative to rest to occur only under hypercapnia; but not under adenosine. For the case in FIG. 19A, rest and stress MBF (under hypercapnia and adenosine) and corresponding MPR are shown as polar maps in FIG. 19B. FIG. 19C shows the MBF at rest before (Caff(−)) and after (Caff(+)) caffeine administration.

FIG. 20A shows the global and regional mean MBF at rest and under hypercapnia and adenosine following caffeine infusion (Caff+). FIG. 20C shows the results from linear regression analysis between regional MBF under adenosine and hypercapnia. FIG. 20B and FIG. 20D show corresponding MPR response. * denotes P<0.05.

DETAILED DESCRIPTION

Figure 1:
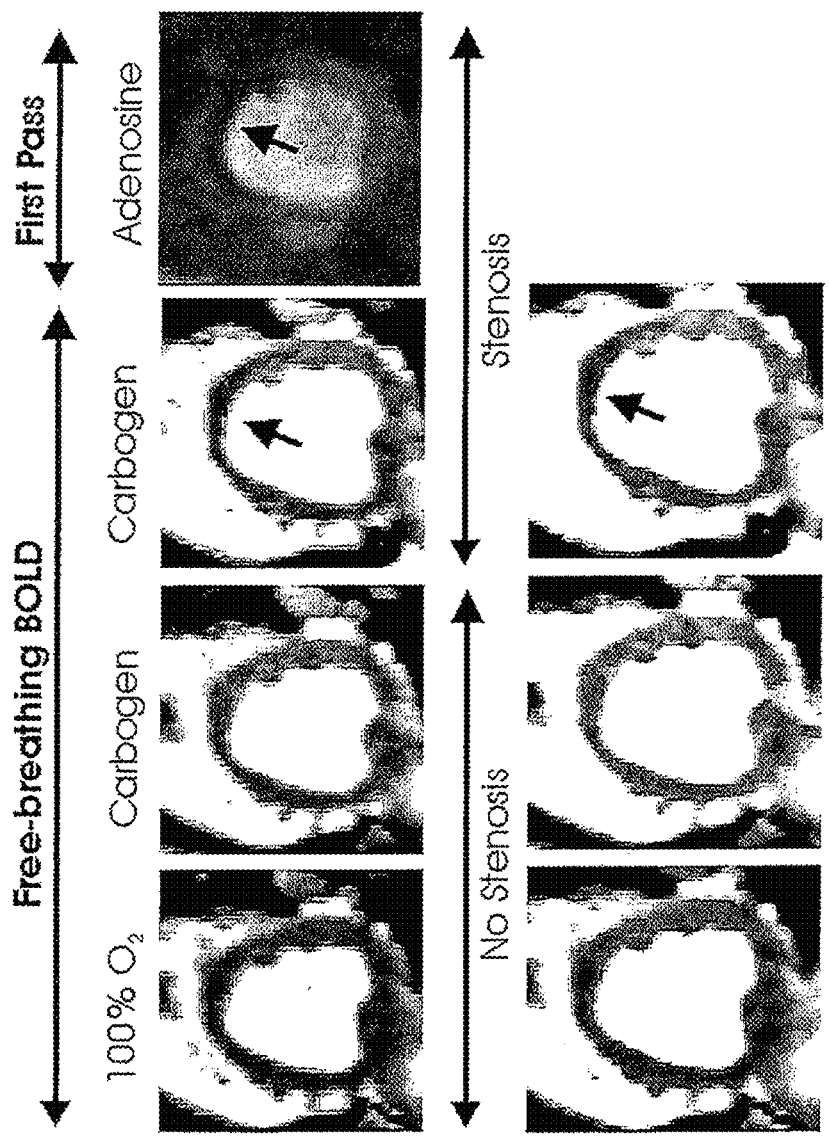
FIG. 1 depicts, in accordance with an embodiment of the present invention, the vascular reactivity in dogs as measured by the BOLD-effect using medical-grade Carbogen (5% $CO_2$ and 95% $O_2$) with and without coronary artery stenosis.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* $3^{rd}$ ed., J. Wiley & Sons (New York, N.Y. 2001); March, *Advanced Organic Chemistry Reactions, Mechanisms and Structure* $5^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Treatment" and "treating," as used herein refer to both therapeutic treatment and prophylactic or preventative measures, wherein the object is to prevent or slow down (lessen) the targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Carbogen" as used herein is an admixture of carbon dioxide and oxygen. The amounts of carbon dioxide and oxygen in the admixture may be determined by one skilled in the art.

Medical grade carbogen is typically 5% $CO_2$ and 95% $O_2$. In various other embodiments, carbon dioxide used to induce hyperemia may be an admixture of ranges including but not limited to 94% $O_2$ and 6% $CO_2$, 93% $O_2$ and 7% $CO_2$, 92% $O_2$ and 8% $CO_2$, 91% $O_2$ and 9% $CO_2$, 90% $O_2$ and 10% $CO_2$, 85% $O_2$ and 15% $CO_2$, 80% $O_2$ and 20% $CO_2$, 75% $O_2$ and 25% $CO_2$ and/or 70% $O_2$ and 30% $CO_2$. Optionally, for blending with air, the $CO_2$ containing gas comprises 20% oxygen.

"BOLD" as used herein refers to blood-oxygen-level dependence.

The term "about" is used herein to indicate that a value includes an inherent variation of error for the device or the method being employed to determine the value.

A "vascular-disease-associated" coronary vasoreactive response means a type and/or quantum of vasoreactive response elicited by cardiac stress testing (e.g. exercise or administration of a hyperemic drug or a $CO_2$ containing gas) as demonstrable in an imaging study using one or more diagnostic imaging parameters of the type suitable to diagnose coronary vascular disease. For example, with respect to PET and SPECT, a normal response would be considered a four to five-fold increase in blood flow. With respect to BOLD MRI imaging, a 10-12+% increase in BOLD signal would be considered normal. Disease associated responses are those which are not normal in varying significant degrees among which, as evidence of disease, benchmarks may be adopted to categorize differences which represent a clearer-cut diagnosis or a progression of disease that warrants greater follow-up or more proactive treatment, for example a less than two-fold increase in blood flow as measured by PET or SPECT (typically measured in ml. of blood/min/gm of tissue). Accordingly, a benchmark which represents a change from a value that clinicians described as "normal" which is at least statistically significant and optionally is also comparable to a standard for cardiac stress testing adopted by clinicians with respect to inducing stress represents a clear-cut benchmark for using $CO_2$ as a vasoactive stress stimulus.

A targeted increase in $PaCO_2$ will be selected to cause a similar vasoreactive response in normal and diseased tissue. From the standpoint of statistical significance, it will be appreciated that selection of a discriminatory increase in $PaCO_2$ may depend on whether or not repeat measurements are made, for example, the number of repeat measurements of a BOLD signal intensity that are made while at lower and increased $PaCO_2$ levels.

Current methods for inducing hyperemia in subjects include the use of compounds such as adenosine, analogs thereof and/or functional equivalents thereof. However, such compounds (for example, adenosine) have adverse side effects including bradycardia, arrhythmia, transient or prolonged episode of asystole, ventricular fibrillation (rarely), chest pain, headache, dyspnea, and nausea, making it less than favorable for initial or follow-up studies.

The technology described herein is directed to the use of $CO_2$ instead of hyperemia-inducing drugs, in view of their side effects, to assess myocardial response and risk of coronary artery diseases. To date, however, it has not been possible to independently control arterial $CO_2$ and $O_2$, hence direct association of the influence of partial pressure of $CO_2$ ($PaCO_2$) on coronary vasodilation has been difficult to determine. With the development of gas flow controller devices designed to control gas concentrations in the lungs and blood (for example, RespirACT™, Thornhill Research, WO/2013/0082703), it is now possible to precisely control the arterial $CO_2$, while, in some embodiments, holding $O_2$ constant. With such devices, the desired $PaCO_2$ changes are rapid (1-2 breaths) and are independent of minute ventilation. The inventors are among the first adopters of such devices for the assessment of myocardial response to $CO_2$.

The methods provided herein are believed to be the first to use modulation of $CO_2$ levels to show that the carbon dioxide can have the same effect as the clinical dose of other hyperemia-inducing drugs such as adenosine but without the side effects. We report herein that hyperemia is induced by administering an admixture comprising a predetermined amount of $CO_2$ to a subject in need thereof to assess myocardial response, evaluate coronary artery disease and identify ischemic heart disease. In an embodiment, hyperemia is induced by independently altering the administered $CO_2$ level while holding oxygen ($O_2$) constant to assess myocardial response, evaluate coronary artery disease and identify ischemic heart disease. A subject's myocardial response after administration of $CO_2$ may be monitored using various imaging techniques such as MRI.

Cardiac Stress Testing

When exercise stress testing is contra-indicated (in nearly 50% of patients), existing imaging modalities use adenosine (or its analogues such as dipyridamole or regadenoson) to induce hyperemia. However, as described above, adenosine or analogs thereof or functional equivalents thereof, are well known for their adverse side effects such as bradycardia, arrhythmia, transient or prolonged episode of asystole, ventricular fibrillation (rarely), chest pain, headache, dyspnea, and nausea, making it less than favorable for initial or follow-up studies. Direct measures of ischemic burden may be determined on the basis of single-photon emission computed tomography (SPECT/SPET), positron emission tomography (PET), myocardial contrast echocardiography (MCE), and first-pass perfusion magnetic resonance imaging (FPP-MRI). SPECT and PET use radiotracers as contrast agents. While SPECT and PET studies account for approximately 90% of myocardial ischemia-testing studies, the sensitivity and specificity for both methods combined for the determination of severe ischemia is below 70%. Both MCE and FPP-MRI are relatively newer approaches that require the use of exogenous contrast media and intravenous pharmacological stress agent (such as adenosine), both carrying significant risks and side effects in certain patient populations.

BOLD-MRI

An alternate method, BOLD (Blood-Oxygen-Level-Dependent) MRI, relies on endogenous contrast mechanisms (changes in blood oxygen saturation, % $O_2$) to identify ischemic territories. The potential benefits of BOLD MRI for detecting global or regional myocardial ischemia due to coronary artery disease (CAD) were demonstrated at least a decade ago. Although a number of pilot clinical studies have demonstrated the feasibility of using BOLD MRI for identifying clinically significant myocardial ischemia due to CAD, the method is inherently limited by sensitivity and specificity due to low BOLD contrast-to-noise ratio (CNR). In some embodiments of methods provided herein, the repeatability of BOLD MRI using $CO_2$ provides the means to improve sensitivity and specificity, which is not possible using adenosine or analogs thereof.

In some embodiments, there is provided a method for increasing the sensitivity and specificity of BOLD MRI. The method includes administering an admixture comprising $CO_2$ to a subject in need thereof to induce hyperemia and imaging the myocardium using MRI to assess a hypermic response in response to a predetermined modulation in $PaCO_2$. In some embodiments, this method utilizes (i) an individualized targeted change in arterial partial pressure of $CO_2$ ($PaCO_2$) as the non-invasive vasoactive stimulus, (ii) fast, high-resolution, 4D BOLD MRI at 3T and (iii) statistical models (for example, the generalized linear model (GLM) theory) to derive statistical parametric maps (SPM) to reliably detect and quantify the prognostically significant ischemic burden through repeated measurements (i.e., in a data-driven fashion). In some embodiments, the method for increasing the sensitivity and specificity of BOLD MRI comprises (i) obtaining free-breathing cardiac phase-resolved 3D myocardial BOLD images (under different $PaCO_2$ states established via inhalation of an admixture of gases comprising of $CO_2$); (ii) registering and segmenting the images to obtain the myocardial dynamic volume; and (iii) identifying ischemic territory and quantifying image volume.

Obtaining the Images

The first step in increasing the sensitivity and specificity of BOLD MRI is to obtain free-breathing cardiac phase resolved 3D myocardial BOLD images. Subjects are placed on the MRI scanner table, ECG leads are placed, and necessary surface coils are positioned.

Subsequently the subjects' hearts are localized and the cardiac shim protocol is prescribed over the whole heart. K-space lines, time stamped for trigger time are collected using cine SSFP acquisition with image acceleration along the long axis. Central k-space lines corresponding to each cardiac phase will be used to derive the center of mass (COM) curves along the z-axis via 1-D fast Fourier transform (FFT). Based on the COM curves, the k-space lines from each cardiac phase will be sorted into 1-30 bins, each corresponding to a respiratory state with the first bin being the reference bin (end-expiration) and the last bin corresponding to end inspiration.

To minimize the artifacts from under sampling, the data will be processed with a 3D filter, followed by re-gridding the k-space lines, application of a spatial mask (to restrict the registration to region of the heart) and performing FFT to obtain the under sampled 3D image for each respiratory bin. Using the end-expiration image as the reference image, images from all bins (except bin 1) are registered using kits such as Insight Tool Kit (freely available from www.itk.org), or an equivalent software platform, in an iterative fashion and the transform parameters will be estimated for rotation, scaling, shearing, and translation of heart between the different respiratory bins. The k-space data will again be divided into 1 to 30 respiratory bins, re-gridded, transformed to the reference image (3D affine transform), summed together, and the final 3D image will be reconstructed. Imaging parameters may be TR=3.0 to 10 ms and flip angle=1° to 90°. In this fashion, 3D cine data under controlled $PaCO_2$ values (hypo- and hyper-carbic states) are collected.

Registration and Segmentation of Images

The next step in increasing the sensitivity and specificity of BOLD MRI is registration and segmentation of the images to obtain the myocardial dynamic volume. The pipeline utilizes MATLAB and C++ using the ITK framework or an equivalent software platform. The myocardial MR images obtained with repeat $CO_2$ stimulation blocks will be loaded in MATLAB (or an equivalent image processing platform) and arranged in a four-dimensional (4D) matrix, where the first 3 dimensions represent volume (voxels) and the fourth dimension is time (cardiac phase). Subsequently, each volume is resampled to achieve isotropic voxel size. End-systole (ES) are identified for each stack based on our minimum cross-correlation approach. A 4D non-linear registration algorithm is used to find voxel-to-voxel correspondences (deformation fields) across all cardiac phases. Using the recovered deformation, all cardiac phases are wrapped to the space of ES, such that all phases are aligned to ES. The next step is to recover the transformations across all ES images from repeat $CO_2$ blocks and bring them to the same space using a diffeomorphic volume registration tool, such as ANTs. Upon completion, all cardiac phases from all acquisitions will be spatially aligned to the space of ES of the first acquisition (used as reference) and all phase-to-phase deformations and acquisition-to-acquisition transformations will be known. An expert delineation of the myocardium in the ES of the first (reference) acquisition will then be performed. Based on the estimated deformation fields and transformations, this segmentation is propagated to all phases and acquisitions, resulting in fully registered and segmented myocardial dynamic volumes.

Image Analysis to Identify and Quantify Ischemic Territories

The final step needed for increasing the sensitivity and specificity of BOLD MRI is identifying ischemic territory and quantifying image volume. Since BOLD responses are optimally observed in systolic frames, only L systolic cardiac volumes (centered at ES) are retained from each fully registered and segmented 4D BOLD MR image set obtained above. Only those voxels contained in the myocardium are retained and the corresponding RPP (rate-pressure-product) and $PaCO_2$ are noted. Assuming N acquisitions per $CO_2$ state (hypocarbic or hypercarbic) and K, $CO_2$ stimulation blocks, and each cardiac volume consists of n×m×p (x=multiplication) isotropic voxels, build a concatenated fully registered 4D dataset consisting of nxmxpxt pixels, where x=multiplication and t=L×K×N, and export this dataset in NIFTI (or an equivalent) format using standard tools. The 4D dataset is loaded into a voxel-based statistical model fitting (such as FSL-FEAT developed for fMRI), to fit the model for each voxel. The statistical analysis outputs a P-statistic volume, i.e., the SPM, where for each voxel in the myocardium the p-value of the significance of the correlation to the model is reported. The statistical parametric maps (SPM) are thresholded by identifying the voxels that have $p<0.05$. Those voxels are identified as hyperemic for responding to the $CO_2$ stimulation. The total number of hyperemic voxels ($V_H$) are counted and their relative volume ($V_{RH}=V_H$/total voxels in myocardium) is determined. The voxels that do not respond to $CO_2$ stimulation (on SPM) are identified as ischemic and used to generate a binary 3D map of ischemic voxels (3D-$ISCH_{map}$). In addition, total ischemic voxels ($V_I$) and the relative ischemic volume ($V_{RI}=V_I$/total myocardial voxels) are determined.

The above methods provide ischemic volumes that can be reliably identified on the basis of statistical analysis applied to repeatedly acquire 4D BOLD images under precisely targeted changes in $PaCO_2$. These volumes are closely related to the clinical index of fractional flow reserve FFR.

FFR

An additional method, fractional flow reserve (FFR) is used in coronary catheterization to measure pressure differences across a coronary artery stenosis to determine the likelihood that the stenosis impedes oxygen delivery to the heart muscle (myocardial ischemia). Fractional flow reserve measures the pressure behind (distal to) a stenosis relative to the pressure before the stenosis, using adenosine or papaverine to induce hyperemia. A cut-off point of 0.75 to 0.80 has been used wherein higher values indicate a non-significant stenosis and lower values indicate a significant lesion. FFR, determined as the relative pressure differences across the stenotic coronary artery has emerged as the new standard for determining clinically significant ischemia (FFR≤0.75). However, it is invasive, expensive, and exposes the patient to ionizing radiation and the side-effects of the use of adenosine. In view of the side-effects of adenosine discussed above, Applicants propose using carbon dioxide instead of adenosine to induce hyperemia, by administering to a subject an admixture comprising $CO_2$ to reach a predetermined $PaCO_2$ in the subject to induce hyperemia. In some embodiments, the admixture comprises any one or more of carbon dioxide, oxygen, and nitrogen, e.g., carbon dioxide, oxygen and nitrogen; carbon dioxide and oxygen; carbon dioxide and nitrogen; or carbon dioxide alone. In one embodiment, the amounts of $CO_2$ and $O_2$ administered are both altered. In another embodiment, the amount of $CO_2$ administered is altered to a predetermined level while the amount of $O_2$ administered is held constant. In various embodiments, the amounts of any one or more of $CO_2$, $O_2$ and $N_2$ in an admixture are changed or held constant as would be readily apparent to a person having ordinary skill in the art.

Methods

There are provided herein methods for diagnosing coronary heart disease in a subject in need thereof comprising administering an admixture comprising $CO_2$ to a subject to reach a predetermined $PaCO_2$ in the subject to induce hyperemia, monitoring vascular reactivity in the subject and diagnosing the presence or absence of coronary heart disease in the subject, wherein decreased vascular reactivity in the subject compared to a control subject is indicative of coronary heart disease. In an embodiment, $CO_2$ is administered via inhalation. In another embodiment, $CO_2$ levels are altered while the $O_2$ levels remain unchanged so that the $PaCO_2$ is changed independently of the $O_2$ level. In a further embodiment, vascular reactivity is monitored using imaging techniques deemed appropriate by one skilled in the art, including but not limited to any one or more of positron emission tomography (PET), single photon emission computed tomography/computed tomography (SPECT), computed tomography (CT), magnetic resonance imaging (MRI), functional magnetic resonance imaging (fMRI), single photon emission computed tomography/computed tomography (SPECT/CT), positron emission tomography/computed tomography (PET/CT), ultrasound, electrocardiogram (ECG), Electron-beam computed tomography (EBCT), echocardiogram (ECHO), and electron spin resonance (ESR), and/or any combination of the imaging modalities such as (PET/MR), PET/CT, and/or SPECT/MR. In an embodiment, vascular reactivity is monitored using free-breathing BOLD MRI. In some embodiments, the admixture comprises any one or more of carbon dioxide, oxygen and nitrogen, e.g., carbon dioxide, oxygen and nitrogen; carbon dioxide and oxygen; carbon dioxide and nitrogen; or carbon dioxide alone. In one embodiment, the amounts of $CO_2$ and $O_2$ administered are both altered. In another embodiment, the amount of $CO_2$ administered is altered to a predetermined level while the amount of $O_2$ administered is held constant. In various embodiments, the amounts of any one or more of $CO_2$, $O_2$ and $N_2$ in an admixture are changed or held constant as would be readily apparent to a person having ordinary skill in the art.

The invention also provides a method for assessing hyperemic response in a subject in need thereof comprising administering an admixture comprising $CO_2$ to a subject to reach a predetermined $PaCO_2$ in the subject to induce hyperemia, monitoring vascular reactivity in the subject and assessing hyperemic response in the subject, wherein decreased vascular reactivity in the subject compared to a control subject is indicative of poor hyperemic response, thereby assessing hyperemic response in the subject in need thereof. This method may also be used to assess organ perfusion and assess vascular reactivity. In an embodiment, $CO_2$ is administered via inhalation. In another embodiment, $CO_2$ levels are altered while the $O_2$ levels remain unchanged so that the $PaCO_2$ is changed independently of the $O_2$ level. In a further embodiment, vascular reactivity is monitored using imagining techniques deemed appropriate by one skilled in the art, including but not limited to any one or more of positron emission tomography (PET), single photon emission computed tomography/computed tomography (SPECT), computed tomography (CT), magnetic resonance imaging (MRI), functional magnetic resonance imaging (fMRI), single photon emission computed tomography/computed tomography (SPECT/CT), positron emission tomography/computed tomography (PET/CT), ultrasound, electrocardiogram (ECG), Electron-beam computed tomography (EBCT), echocardiogram (ECHO), and electron spin resonance (ESR), and/or any combination of the imaging modalities such as (PET/MR), PET/CT, and/or SPECT/MR. In an embodiment, vascular reactivity is monitored using free-breathing BOLD MRI. In some embodiments, the admixture comprises any one or more of carbon dioxide, oxygen and nitrogen, e.g., carbon dioxide, oxygen and nitrogen; carbon dioxide and oxygen; carbon dioxide and nitrogen; or carbon dioxide alone. In one embodiment, the amounts of $CO_2$ and $O_2$ administered are both altered. In another embodiment, the amount of $CO_2$ administered is altered to a predetermined level while the amount of $O_2$ administered is held constant. In various embodiments, the amounts of any one or more of $CO_2$, $O_2$ and $N_2$ in an admixture are changed or held constant as would be readily apparent to a person having ordinary skill in the art.

The invention is further directed to methods for producing coronary vasodilation in a subject in need thereof comprising providing a composition comprising $CO_2$ and administering the composition comprising $CO_2$ to a subject to reach a predetermined $PaCO_2$ in the subject so as to produce coronary vasodilation in the subject, thereby producing coronary vasodilation in the subject. In an embodiment, $CO_2$ is administered via inhalation. In another embodiment, $CO_2$ levels are altered while the $O_2$ levels remain unchanged so that the $PaCO_2$ is changed independently of the $O_2$ level. In a further embodiment, vascular reactivity is monitored using imagining techniques deemed appropriate by one skilled in the art, including but not limited to any one or more of positron emission tomography (PET), single photon emission computed tomography/computed tomography (SPECT), computed tomography (CT), magnetic resonance imaging (MRI), functional magnetic resonance imaging (fMRI), single photon emission computed tomography/computed tomography (SPECT/CT), positron emission tomography/computed tomography (PET/CT), ultrasound, electrocardiogram (ECG), Electron-beam computed tomography (EBCT), echocardiogram (ECHO), and electron spin resonance (ESR) and/or any combination of the imaging modalities such as (PET/MR), PET/CT, and/or SPECT/MR. In an embodiment, vascular reactivity is monitored using free-breathing BOLD MRI. In some embodiments, the admixture comprises any one or more of carbon dioxide, oxygen and nitrogen, e.g., carbon dioxide, oxygen and nitrogen; carbon dioxide and oxygen; carbon dioxide and nitrogen; or carbon dioxide alone. In one embodiment, the amounts of $CO_2$ and $O_2$ administered are both altered. In another embodiment, the amount of $CO_2$ administered is altered to a predetermined level while the amount of $O_2$ administered is held constant. In various embodiments, the amounts of any one or more of $CO_2$, $O_2$ and $N_2$ in an admixture are changed or held constant as would be readily apparent to a person having ordinary skill in the art.

The invention also provides a method for assessing tissue and/or organ perfusion in a subject in need thereof comprising administering an admixture comprising $CO_2$ to a subject to reach a predetermined $PaCO_2$ in the subject to induce hyperemia, monitoring vascular reactivity in the tissue and/or organ and assessing tissue and/or organ perfusion by assessing the hyperemic response in the subject, wherein decreased vascular reactivity in the subject compared to a control subject is indicative of poor hyperemic response and therefore poor tissue and/or organ perfusion. In an embodiment, $CO_2$ is administered via inhalation. In another embodiment, $CO_2$ levels are altered while the $O_2$ levels remain unchanged so that the $PaCO_2$ is changed independently of the $O_2$ level. In a further embodiment, vascular reactivity is monitored using imagining techniques deemed appropriate by one skilled in the art, including but not limited to any one or more of positron emission tomography (PET), single photon emission computed tomography/computed tomography (SPECT), computed tomography (CT), magnetic resonance imaging (MRI), functional magnetic resonance imaging (fMRI), single photon emission computed tomography/computed tomography (SPECT/CT), positron emission tomography/computed tomography (PET/CT), ultrasound, electrocardiogram (ECG), Electron-beam computed tomography (EBCT), echocardiogram (ECHO), and electron spin resonance (ESR), and/or any combination of the imaging modalities such as (PET/MR), PET/CT, and/or SPECT/MR. In an embodiment, vascular reactivity is monitored using free-breathing BOLD MRI. In some embodiments, the admixture comprises any one or more of carbon dioxide, oxygen and nitrogen, e.g., carbon dioxide, oxygen and nitrogen; carbon dioxide and oxygen; carbon dioxide and nitrogen; or carbon dioxide alone. In one embodiment, the amounts of $CO_2$ and $O_2$ administered are both altered. In another embodiment, the amount of $CO_2$ administered is altered to a predetermined level while the amount of $O_2$ administered is held constant. In various embodiments, the amounts of any one or more of $CO_2$, $O_2$ and $N_2$ in an admixture are changed or held constant as would be readily apparent to a person having ordinary skill in the art.

In some embodiments, the admixture comprising $CO_2$ is administered at high doses for short duration or at low doses for longer durations. For example, administering the admixture comprising $CO_2$ at high doses of $CO_2$ for a short duration comprises administering any one or more of 40 mmHg to 45 mmHg, 45 mmHg to 50 mmHg, 50 mmHg to 55 mmHg, 55 mmHg $CO_2$ to 60 mm Hg $CO_2$, 60 mmHg $CO_2$ to 65 mm Hg $CO_2$, 65 mmHg $CO_2$ to 70 mm Hg $CO_2$, 70 mmHg $CO_2$ to 75 mm Hg $CO_2$, 75 mmHg $CO_2$ to 80 mm Hg $CO_2$, 80 mmHg $CO_2$ to 85 mm Hg $CO_2$ or a combination thereof, for about 20 minutes, 15 minutes, 10 minutes, 9 minutes, 8 minutes, 7 minutes, 6 minutes, 5 minutes, 4 minutes, 3 minutes, 2 minutes, 1 minute or a combination thereof. In various embodiments, the predetermined levels of $CO_2$ are administered so that the arterial level of $CO_2$ reaches the $PaCO_2$ of any one or more of the above ranges. In an embodiment, the predetermined levels of $CO_2$ are administered so that the arterial level of $CO_2$ reaches the $PaCO_2$ of about 60 mm Hg.

For example, administering low doses of predetermined amounts of $CO_2$ for a longer duration comprises administering the predetermined amount of $CO_2$ at any one or more of about 30 mmHg $CO_2$ to about 35 mmHg $CO_2$, about 35 mmHg $CO_2$ to about 40 mmHg $CO_2$, about 40 mmHg $CO_2$ to about 45 mmHg $CO_2$, about 60 mmHg $CO_2$ to about 65 mmHg $CO_2$, or a combination thereof for any one or more of about 20 to 24 hours, about 15 to 20 hours, about 10 to 15 hours, about 5 to 10 hours, about 4 to 5 hours, about 3 to 4 hours, about 2 to 3 hours, and about 1 to 2 hours, or a combination thereof, before inducing hyperemia. In various embodiments, the predetermined levels of $CO_2$ are administered so that the arterial level of $CO_2$ reaches the $PaCO_2$ of any one or more of the above ranges.

In still further embodiments, the predetermined levels of $CO_2$ are administered so that the arterial level of $CO_2$ reaches a $PaCO_2$ that is increased by about 25 mmHg in a subject, i.e., an about 25 mm Hg increase in $PaCO_2$ is achieved in the subject after the $CO_2$ administration. In an embodiment, the predetermined levels of $CO_2$ are administered so that the arterial level of $CO_2$ reaches the $PaCO_2$ of about 60 mm Hg. For example, $PaCO_2$ may be altered from a baseline level of about 35 mm Hg to about 60 mm Hg in the subject. In some embodiments, the $PaCO_2$ is increased by about 22 mm Hg to about 28 mm Hg in the subject, or by about 22 mm Hg, about 23 mm Hg, about 24 mm Hg, about 25 mm Hg, about 26 mm Hg, about 27 mm Hg, or about 28 mm Hg in the subject.

In some embodiments, the predetermined levels of $CO_2$ are administered so that the hyperemic response in the subject is an about two-fold increase in the subject's myocardial blood flow relative to a measured baseline value in the subject (e.g., value before administration of $CO_2$).

In some embodiments, the predetermined levels of $CO_2$ are administered so that the hyperemic response in the subject is substantially the same as the hyperemic response obtained using a hyperemia-inducing drug such as adenosine, e.g., is substantially the same as a reference standard. In some embodiments, the predetermined levels of $CO_2$ are selected to induce a selected hyperemic response in the subject. In some embodiments, the selected hyperemic response is a reference standard hyperemic response. In some embodiments, the selected hyperemic response is a hyperemic response that is sufficient to show a response deficit in ischemic tissue, i.e. sufficient to enable imaging of a reduced hyperemic response in ischemic tissue in at least one segment of the subject's myocardium in a cardiac imaging procedure.

In one embodiment, $CO_2$ is administered in a stepwise manner. In another embodiment, administering carbon dioxide in a stepwise manner includes administering carbon dioxide in 5 mmHg increments in the range of any one or more of 10 mmHg to 100 mmHg $CO_2$, 20 mmHg to 100 mmHg $CO_2$, 30 mmHg to 100 mmHg $CO_2$, 40 mmHg to 100 mmHg $CO_2$, 50 mmHg to 100 mmHg $CO_2$, 60 mmHg to 100 mmHg $CO_2$, 10 mmHg to 90 mmHg $CO_2$, 20 mmHg to 90 mmHg $CO_2$, 30 mmHg to 90 mmHg $CO_2$, 40 mmHg to 90 mmHg $CO_2$, 50 mmHg to 90 mmHg $CO_2$, 60 mmHg to 90 mmHg $CO_2$, 10 mmHg to 80 mmHg $CO_2$, 20 mmHg to 80 mmHg $CO_2$, 30 mmHg to 80 mmHg $CO_2$, 40 mmHg to 80 mmHg $CO_2$, 50 mmHg to 80 mmHg $CO_2$, 60 mmHg to 80 mmHg $CO_2$, 10 mmHg to 70 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 60 mmHg $CO_2$, 30 mmHg to 60 mmHg $CO_2$, 40 mmHg to 60 mmHg $CO_2$ and 50 mmHg to 60 mmHg $CO_2$. In various embodiments, the predetermined levels of $CO_2$ are administered so that the arterial level of $CO_2$ reaches the $PaCO_2$ of any one or more of the above ranges.

In another embodiment, administering carbon dioxide in a stepwise manner includes administering carbon dioxide in 10 mmHg increments in the range of any one or more of 10 mmHg to 100 mmHg $CO_2$, 20 mmHg to 100 mmHg $CO_2$, 30 mmHg to 100 mmHg $CO_2$, 40 mmHg to 100 mmHg $CO_2$, 50 mmHg to 100 mmHg $CO_2$, 60 mmHg to 100 mmHg $CO_2$, 10 mmHg to 90 mmHg $CO_2$, 20 mmHg to 90 mmHg $CO_2$, 30 mmHg to 90 mmHg $CO_2$, 40 mmHg to 90 mmHg $CO_2$, 50 mmHg to 90 mmHg $CO_2$, 60 mmHg to 90 mmHg $CO_2$, 10 mmHg to 80 mmHg $CO_2$, 20 mmHg to 80 mmHg $CO_2$, 30 mmHg to 80 mmHg $CO_2$, 40 mmHg to 80 mmHg $CO_2$, 50 mmHg to 80 mmHg $CO_2$, 60 mmHg to 80 mmHg $CO_2$, 10 mmHg to 70 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 60 mmHg $CO_2$, 30 mmHg to 60 mmHg $CO_2$, 40 mmHg to 60 mmHg $CO_2$ and 50 mmHg to 60 mmHg $CO_2$. In various embodiments, the predetermined levels of $CO_2$ are administered so that the arterial level of $CO_2$ reaches the $PaCO_2$ of any one or more of the above ranges.

In a further embodiment, administering carbon dioxide in a stepwise manner includes administering carbon dioxide in 20 mmHg increments in the range of any one or more of 10 mmHg to 100 mmHg $CO_2$, 20 mmHg to 100 mmHg $CO_2$, 30 mmHg to 100 mmHg $CO_2$, 40 mmHg to 100 mmHg $CO_2$, 50 mmHg to 100 mmHg $CO_2$, 60 mmHg to 100 mmHg $CO_2$, 10 mmHg to 90 mmHg $CO_2$, 20 mmHg to 90 mmHg $CO_2$, 30 mmHg to 90 mmHg $CO_2$, 40 mmHg to 90 mmHg $CO_2$, 50 mmHg to 90 mmHg $CO_2$, 60 mmHg to 90 mmHg $CO_2$, 10 mmHg to 80 mmHg $CO_2$, 20 mmHg to 80 mmHg $CO_2$, 30 mmHg to 80 mmHg $CO_2$, 40 mmHg to 80 mmHg $CO_2$, 50 mmHg to 80 mmHg $CO_2$, 60 mmHg to 80 mmHg $CO_2$, 10 mmHg to 70 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 60 mmHg $CO_2$, 30 mmHg to 60 mmHg $CO_2$, 40 mmHg to 60 mmHg $CO_2$ and 50 mmHg to 60 mmHg $CO_2$. In various embodiments, the predetermined levels of $CO_2$ are administered so that the arterial level of $CO_2$ reaches the $PaCO_2$ of any one or more of the above ranges.

In a further embodiment, administering carbon dioxide in a stepwise manner includes administering carbon dioxide in 25 mmHg increments in the range of any one or more of 10 mmHg to 100 mmHg $CO_2$, 20 mmHg to 100 mmHg $CO_2$, 30 mmHg to 100 mmHg $CO_2$, 40 mmHg to 100 mmHg $CO_2$, 50 mmHg to 100 mmHg $CO_2$, 60 mmHg to 100 mmHg $CO_2$, 10 mmHg to 90 mmHg $CO_2$, 20 mmHg to 90 mmHg $CO_2$, 30 mmHg to 90 mmHg $CO_2$, 40 mmHg to 90 mmHg $CO_2$, 50 mmHg to 90 mmHg $CO_2$, 60 mmHg to 90 mmHg $CO_2$, 10 mmHg to 80 mmHg $CO_2$, 20 mmHg to 80 mmHg $CO_2$, 30 mmHg to 80 mmHg $CO_2$, 40 mmHg to 80 mmHg $CO_2$, 50 mmHg to 80 mmHg $CO_2$, 60 mmHg to 80 mmHg $CO_2$, 10 mmHg to 70 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 60 mmHg $CO_2$, 30 mmHg to 60 mmHg $CO_2$, 40 mmHg to 60 mmHg $CO_2$ and 50 mmHg to 60 mmHg $CO_2$. In various embodiments, the predetermined levels of $CO_2$ are administered so that the arterial level of $CO_2$ reaches the $PaCO_2$ of any one or more of the above ranges.

In a further embodiment, administering carbon dioxide in a stepwise manner includes administering carbon dioxide in 30 mmHg increments in the range of any one or more of 10 mmHg to 100 mmHg $CO_2$, 20 mmHg to 100 mmHg $CO_2$, 30 mmHg to 100 mmHg $CO_2$, 40 mmHg to 100 mmHg $CO_2$, 50 mmHg to 100 mmHg $CO_2$, 60 mmHg to 100 mmHg $CO_2$, 10 mmHg to 90 mmHg $CO_2$, 20 mmHg to 90 mmHg $CO_2$, 30 mmHg to 90 mmHg $CO_2$, 40 mmHg to 90 mmHg $CO_2$, 50 mmHg to 90 mmHg $CO_2$, 60 mmHg to 90 mmHg $CO_2$, 10 mmHg to 80 mmHg $CO_2$, 20 mmHg to 80 mmHg $CO_2$, 30 mmHg to 80 mmHg $CO_2$, 40 mmHg to 80 mmHg $CO_2$, 50 mmHg to 80 mmHg $CO_2$, 60 mmHg to 80 mmHg $CO_2$, 10 mmHg to 70 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 60 mmHg $CO_2$, 30 mmHg to 60 mmHg $CO_2$, 40 mmHg to 60 mmHg $CO_2$ and 50 mmHg to 60 mmHg $CO_2$. In various embodiments, the predetermined levels of $CO_2$ are administered so that the arterial level of $CO_2$ reaches the $PaCO_2$ of any one or more of the above ranges.

In a further embodiment, administering carbon dioxide in a stepwise manner includes administering carbon dioxide in 40 mmHg increments in the range of any one or more of 10 mmHg to 100 mmHg $CO_2$, 20 mmHg to 100 mmHg $CO_2$, 30 mmHg to 100 mmHg $CO_2$, 40 mmHg to 100 mmHg $CO_2$, 50 mmHg to 100 mmHg $CO_2$, 60 mmHg to 100 mmHg $CO_2$, 10 mmHg to 90 mmHg $CO_2$, 20 mmHg to 90 mmHg $CO_2$, 30 mmHg to 90 mmHg $CO_2$, 40 mmHg to 90 mmHg $CO_2$, 50 mmHg to 90 mmHg $CO_2$, 60 mmHg to 90 mmHg $CO_2$, 10 mmHg to 80 mmHg $CO_2$, 20 mmHg to 80 mmHg $CO_2$, 30 mmHg to 80 mmHg $CO_2$, 40 mmHg to 80 mmHg $CO_2$, 50 mmHg to 80 mmHg $CO_2$, 60 mmHg to 80 mmHg $CO_2$, 10 mmHg to 70 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 60 mmHg $CO_2$, 30 mmHg to 60 mmHg $CO_2$, 40 mmHg to 60 mmHg $CO_2$ and 50 mmHg to 60 mmHg $CO_2$. In various embodiments, the predetermined levels of $CO_2$ are administered so that the arterial level of $CO_2$ reaches the $PaCO_2$ of any one or more of the above ranges.

In a further embodiment, administering carbon dioxide in a stepwise manner includes administering carbon dioxide in 50 mmHg increments in the range of any one or more of 10 mmHg to 100 mmHg $CO_2$, 20 mmHg to 100 mmHg $CO_2$, 30 mmHg to 100 mmHg $CO_2$, 40 mmHg to 100 mmHg $CO_2$, 50 mmHg to 100 mmHg $CO_2$, 60 mmHg to 100 mmHg $CO_2$, 10 mmHg to 90 mmHg $CO_2$, 20 mmHg to 90 mmHg $CO_2$, 30 mmHg to 90 mmHg $CO_2$, 40 mmHg to 90 mmHg $CO_2$, 50 mmHg to 90 mmHg $CO_2$, 60 mmHg to 90 mmHg $CO_2$, 10 mmHg to 80 mmHg $CO_2$, 20 mmHg to 80 mmHg $CO_2$, 30 mmHg to 80 mmHg $CO_2$, 40 mmHg to 80 mmHg $CO_2$, 50 mmHg to 80 mmHg $CO_2$, 60 mmHg to 80 mmHg $CO_2$, 10 mmHg to 70 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 60 mmHg $CO_2$, 30 mmHg to 60 mmHg $CO_2$, 40 mmHg to 60 mmHg $CO_2$ and 50 mmHg to 60 mmHg $CO_2$. In various embodiments, the predetermined levels of $CO_2$ are administered so that the arterial level of $CO_2$ reaches the $PaCO_2$ of any one or more of the above ranges.

Other increments of carbon dioxide to be administered in a stepwise manner will be readily apparent to a person having ordinary skill in the art.

In a further embodiment, a predetermined amount of $CO_2$ is administered in a block manner. Block administration of carbon dioxide comprises administering carbon dioxide in alternating amounts over a period of time. "In alternating amounts" of $CO_2$ comprises alternating between any of 20 mmHg and 40 mmHg, 30 mmHg and 40 mmHg, 20 mmHg and 50 mmHg, 30 mmHg and 50 mmHg, 40 mmHg and 50 mmHg, 20 mmHg and 60 mmHg, 30 mmHg and 60 mmHg, 40 mmHg and 60 mmHg, and 50 mmHg and 60 mmHg. In various embodiments, the predetermined levels of $CO_2$ are administered so that the arterial level of $CO_2$ reaches the $PaCO_2$ of any one or more of the above ranges. Other amounts of carbon dioxide to be used in alternating amounts over a period of time will be readily apparent to a person having ordinary skill in the art.

In one embodiment, vascular reactivity may be measured by characterization of Myocardial Perfusion Reserve, which is defined as a ratio of Myocardial Perfusion at Stress to Myocardial Perfusion at Rest. In healthy subjects the ratio may vary from 5:1 to 6:1. The ratio diminishes with disease. A decrease in this ratio to 2:1 from the healthy level is considered to be clinically significant and indicative of poor vascular reactivity.

In another embodiment, vascular reactivity may be measured via differential absolute perfusion, which may be obtained using imaging methods such as first pass perfusion, SPECT/PET, CT perfusion or echocardiography in units of ml/sec/g of tissue.

In an embodiment the $CO_2$ gas is administered via inhalation. $CO_2$ may be administered using, for example, RespirACT™ technology from Thornhill Research. In various embodiments, $CO_2$ is administered for 1-2 minutes, 2-4 minutes, 4-6 minutes, 6-8 minutes, 8-10 minutes, 10-12 minutes, 12-14 minutes, 14-16 minutes, 16-18 minutes and/or 18-20 minutes. In one embodiment, $CO_2$ is administered for 4-6 minutes. In an additional embodiment, $CO_2$ is administered for an amount of time it takes for the arterial $PaCO_2$ (partial pressure of carbon dioxide) to reach 50-60 mmHg from the standard levels of 30 mmHg during $CO_2$-enhanced imaging.

In one embodiment, carbon dioxide used to induce hyperemia is medical-grade carbogen which is an admixture of 95% $O_2$ and 5% $CO_2$. In various other embodiments, carbon dioxide used to induce hyperemia may be an admixture of ranges including but not limited to 94% $O_2$ and 6% $CO_2$, 93% $O_2$ and 7% $CO_2$, 92% $O_2$ and 8% $CO_2$, 91% $O_2$ and 9% $CO_2$, 90% $O_2$ and 10% $CO_2$, 85% $O_2$ and 15% $CO_2$, 80% $O_2$ and 20% $CO_2$, 75% $O_2$ and 25% $CO_2$ and/or 70% $O_2$ and 30% $CO_2$.

In another embodiment, vascular reactivity and/or vasodilation are monitored using any one or more of positron emission tomography (PET), single photon emission computed tomography/computed tomography (SPECT), computed tomography (CT), magnetic resonance imaging (MRI), functional magnetic resonance imaging (fMRI), single photon emission computed tomography/computed tomography (SPECT/CT), positron emission tomography/computed tomography (PET/CT), ultrasound, electrocardiogram (ECG), Electron-beam computed tomography (EBCT), echocardiogram (ECHO), and electron spin resonance (ESR), and/or any combination of the imaging modalities such as (PET/MR), PET/CT, and/or SPECT/MR In an embodiment, vascular reactivity is monitored using free-breathing BOLD MRI.

Imaging techniques using carbon dioxide involve a free-breathing approach so as to permit entry of $CO_2$ into the subject's system. In an embodiment, the subjects include mammalian subjects, including, human, monkey, ape, dog, cat, cow, horse, goat, pig, rabbit, mouse and rat. In a preferred embodiment, the subject is human. It should be noted that the terms "subject" and "patient" are used interchangeably herein.

Advantages of the Invention

The methods described herein to functionally assess the oxygen status of the myocardium include administering an effective amount of $CO_2$ to a subject in need thereof. In an embodiment, the $O_2$ level is held constant while the $CO_2$ level is altered so as to induce hyperemia. Applicants herein show the vascular reactivity in subjects in response to changes in $PaCO_2$. The existing methods use adenosine, dipyridamole, or regadenoson which have significant side-effects, as described above. As described in the Examples below, in some embodiments $CO_2$ is at least as effective as the existing methods (which use, for example, adenosine) but without the side effects. Methods described herein may provide one or more of the following advantages.

The use of $CO_2$ can provide distinct advantages over the use of, for example, adenosine. Administering $CO_2$ is truly non-invasive because it merely involves inhaling physiologically sound levels of $CO_2$. The instant methods are simple, repeatable and fast and most likely have the best chance for reproducibility. Not even breath-holding is necessary during acquisition of images using the methods described herein. The instant methods can also be highly cost-effective as no pharmacological stress agents are required, cardiologists may not need to be present during imaging and rapid imaging reduces scan times and costs. Further, in some embodiments $CO_2$ can produce a selected hyperemic response despite consumption of caffeine, which is advantageous compared to some hyperemia-inducing drugs which do not produce reliable assessments in subjects who have consumed caffeine beforehand.

Further, the improved BOLD MRI technique described above can provide a non-invasive and reliable determination of ischemic volume (no radiation, contrast-media, or adenosine) and other value-added imaging biomarkers from the same acquisition (Ejection Fraction, Wall Thickening). Additionally, the subject does not experience adenosine-related adverse side effects and thus greater patient tolerance for repeat ischemia testing is achieved. In some embodiments, there is a significant cost-savings from abandoning exogenous contrast media and adenosine/regadenoson. Moreover, the proposed BOLD MRI paradigm can be accompanied by significant technical advances as well: (i) a fast, high-resolution, free-breathing 4D SSFP MRI at 3T, that can impact cardiac MRI in general; (ii) Repeated stimulations of the heart via precisely targeted changes in $PaCO_2$; and (iii) adoption of sophisticated analytical methods employed in the brain to the heart.

EXAMPLES

In Examples 1-6, all imaging studies were performed in instrumented animals with a Doppler flow probe attached to the LAD coronary arteries for measurement of flow changes in response to $CO_2$ and clinical dose of adenosine. In these studies, $CO_2$ and $O_2$ delivery were tightly controlled using Respiract. $CO_2$ values were incremented in steps of 10 mmHg starting from 30 mmHg to 60 mmHg and were ramped down in decrements of 10 mmHg. At each $CO_2$ level, free-breathing and cardiac gated blood-oxygen-level-dependent (BOLD) acquisitions were prescribed at mid diastole and Doppler flow velocities were measured. Similar acquisitions were also performed with block sequences of $CO_2$ levels; that is, $CO_2$ levels were alternated between 40 and 50 mmHg and BOLD images (and corresponding Doppler flow velocities) were acquired at each $CO_2$ level to assess the reproducibility of the signal changes associated with different $CO_2$ levels. Each delivery of $CO_2$ using Respiract was made in conjunction with arterial blood draw to determine the arterial blood $CO_2$ levels. Imaging-based demonstration of myocardial hyperemic response to changes in $PaCO_2$ was shown in health human volunteers with informed consent.

Example 1

We show that $CO_2$ can increase myocardial perfusion by a similar amount, as does adenosine in canine models. We also show that in the setting of coronary artery narrowing, it is possible to detect regional variations in hyperemic response with the use of MRI by detecting signal changes in the myocardium due to changes in oxygen saturation (also known as the BOLD effect) using a free-breathing BOLD MRI approach.

As show in FIG. 1, a 20% BOLD signal increase (hyperemic response) with medical-grade carbogen breathing in the absence of stenosis in dogs was observed. With a severe stenosis, the hyperemic response was significantly reduced in the LAD (left anterior descending) territory but the other regions showed an increase in signal intensity (as observed with adenosine). First-pass perfusion images acquired with adenosine under severe stenosis (in the same slice position and trigger time) is also shown for comparison. Heart rate increase of around 5-10% and a drop in blood pressure (measured invasively) by about 5% was also observed in this animal under carbogen. All acquisitions were navigator gated T2-prep 2D SSFP (steady-state free precession) and triggered at mid/end diastole (acquisition window of 50 ms). 10 dogs have been studied with medical-grade carbogen and have yielded highly reproducible results.

In detail, the color images (lower panel of FIG. 1) are color-coded to the signal intensities of grayscale images (above). The darker colors (blue/black) represent territories of baseline myocardial oxygenation and the brighter regions represent those regions that are hyperemic. On average the signal difference between a dark blue (low signal) and orange color (high signal) is about 20%. Note that in the absence of stenosis, as one goes from 100% $O_2$ to Carbogen, the BOLD signal intensity was elevated (second image from left) suggesting $CO_2$ based vasoreactivity of the myocardium. The dogs were instrumented with an occluder over the left-anterior descending (LAD) coronary artery. As the LAD is occluded, note that the region indicated by an arrow (i.e. approximately between 11 o'clock and 1-2 o'clock (region supplied by the LAD)) becomes darker (3rd image from left), suggesting that vasodilation was no longer possible or was reduced. The first pass image (obtained with adenosine stress following BOLD images) at the same stenosis level also shows this territory clearly. We have also compared the epicardial flow enhancements in response to Carbogen (with ETCO2 reaching 48-50 mm Hg) against clinical dose of adenosine and the responses have been quite similar (~20% response).

Example 2

Co-Relation between Inhaled $CO_2$ and Oxygen Saturation

We assessed the difference between myocardial blood-oxygen-level dependent (BOLD) response under hypercarbia and normocarbia conditions in canines. The BOLD signal intensity is proportional to oxygen saturation.

Figure 2:
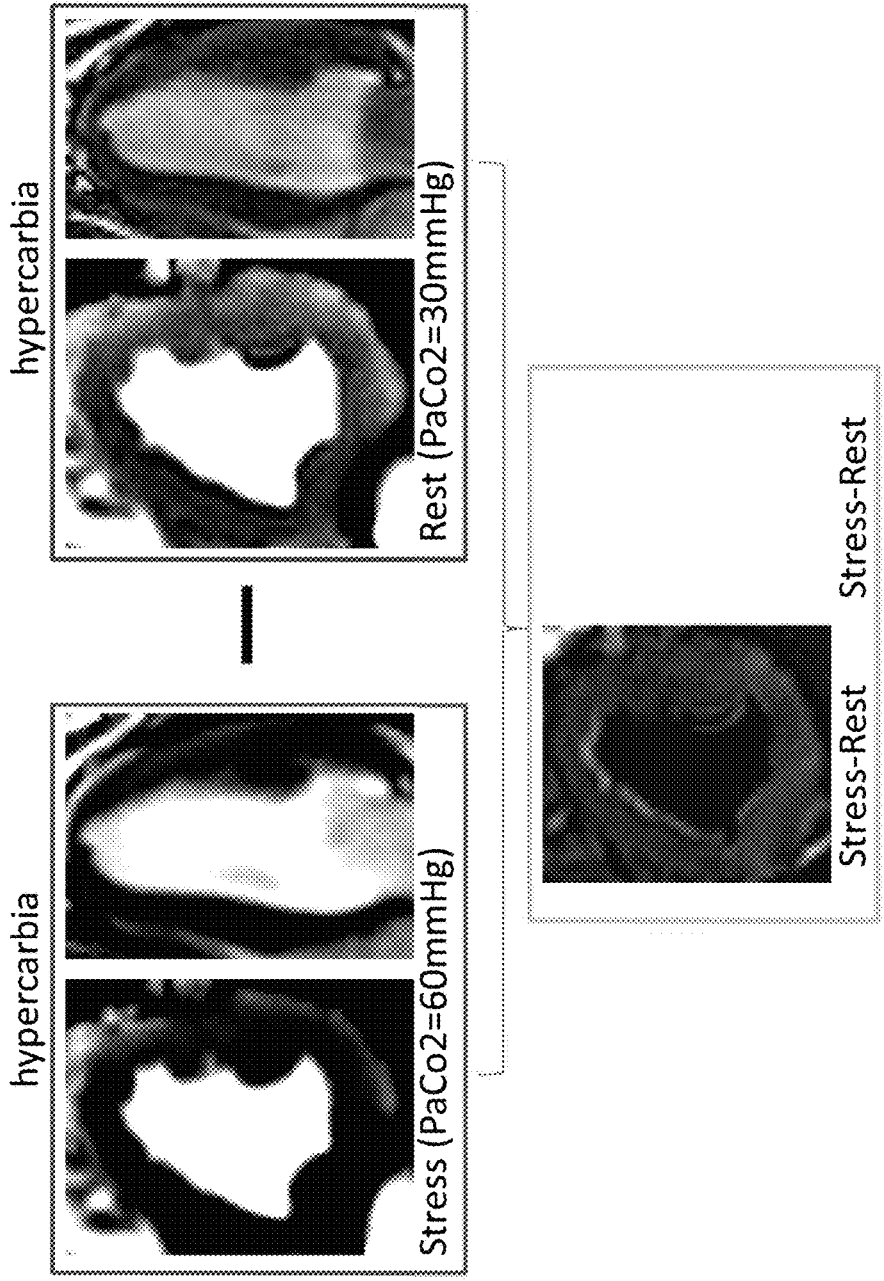
FIG. 2 depicts myocardial BOLD MRI with $CO_2$ in canines under normocarbic and hypercarbic conditions under free breathing conditions.

Top panels of FIG. 2 depict the myocardial response under hypercarbia (60 mm Hg) and normocarbia (30 mmHg) conditions and show an increase in BOLD signal intensity under hypercarbia condition. The lower panel depicts the difference as obtained by subtracting the signal under rest from that under stress. The myocardial BOLD signal difference between the two is depicted in grey and shows the responsiveness of canines to hypercarbia conditions.

Figure 3:
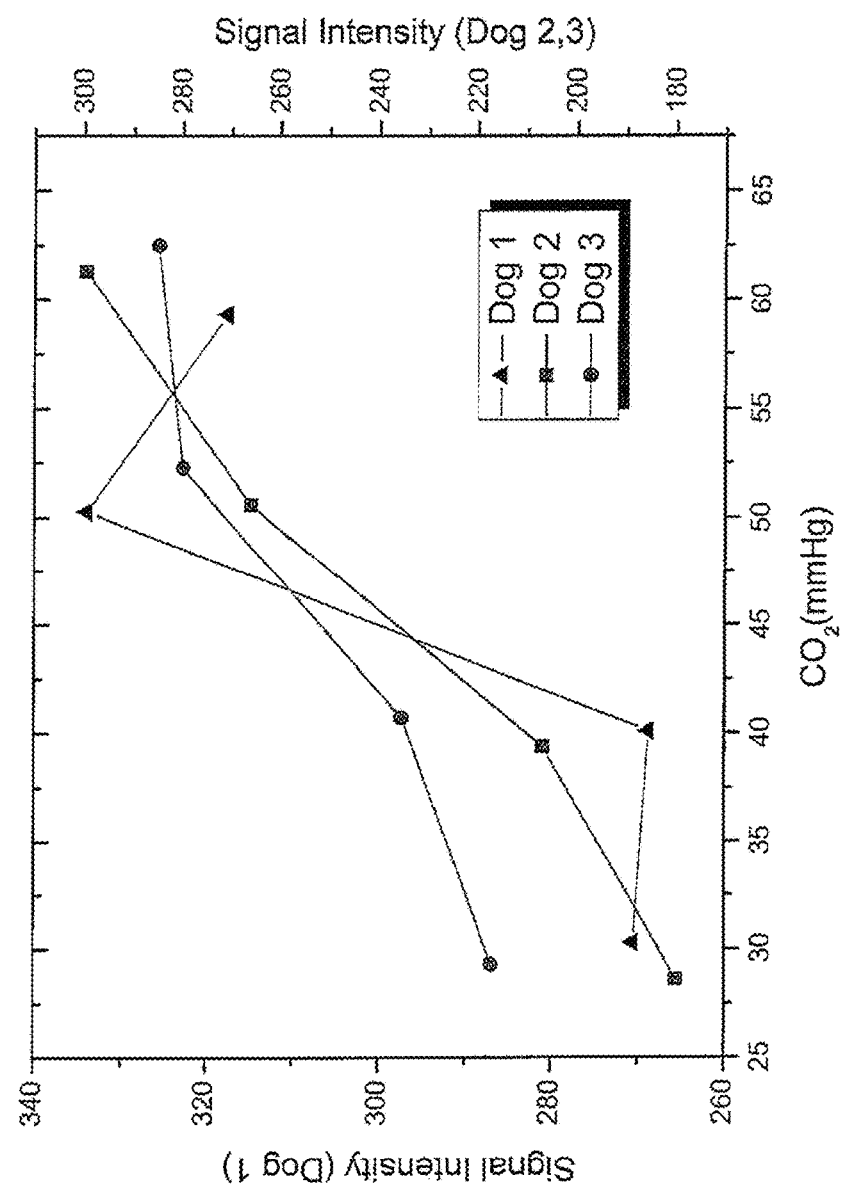
FIG. 3 depicts myocardial BOLD response to step-wise $PaCO_2$ ramp up in canines while holding basal $PaO_2$ constant.

We further assessed the myocardial BOLD response to stepwise $CO_2$ increase (ramp-up) in canines. As shown in FIG. 3, as the amount of $CO_2$ administered increases, the BOLD signal intensity increases which is indicative of an increase in hyperemic response to increased uptake of $CO_2$ and oxygen saturation.

Figure 4:
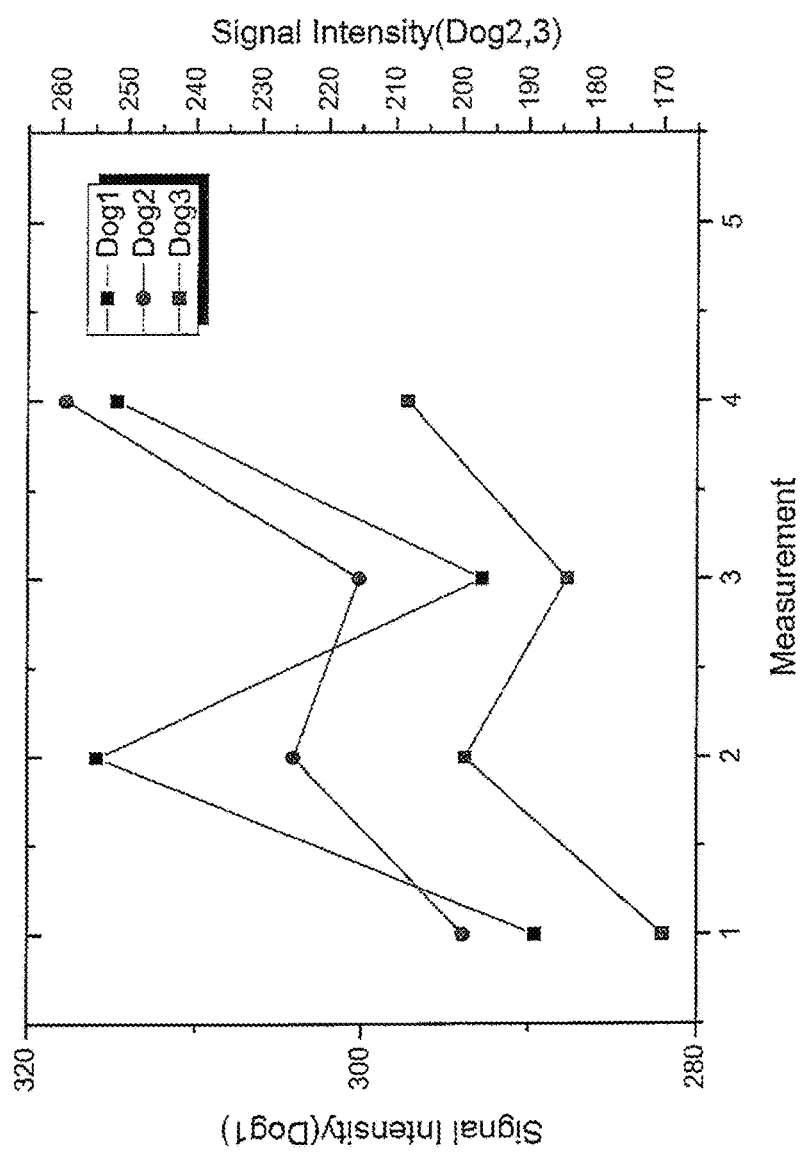
FIG. 4 depicts myocardial BOLD response to repeated (block) administration $CO_2$ response.

To further evaluate vascular reactivity and coronary response to $CO_2$, we measured the myocardial BOLD signal in response to block increases of $CO_2$ in canines. Specifically, the myocardial BOLD signal was measured as the amount of $CO_2$ administered to the canine subjects alternated between 40 mmHg $CO_2$ and 50 mmHg $CO_2$. As shown in FIG. 4, an increase in $CO_2$ level from 40 mmHg $CO_2$ to 50 mmHg $CO_2$ resulted in an increase in BOLD signal intensity and the subsequent decrease in $CO_2$ level to 40 mmHg resulted in a decreased BOLD signal. These results show a tight co-relation between administration of $CO_2$ and vascular reactivity and coronary response.

Example 3

Co-Relation Between the Amount of $CO_2$ Inhaled and Doppler Flow

Figure 5:
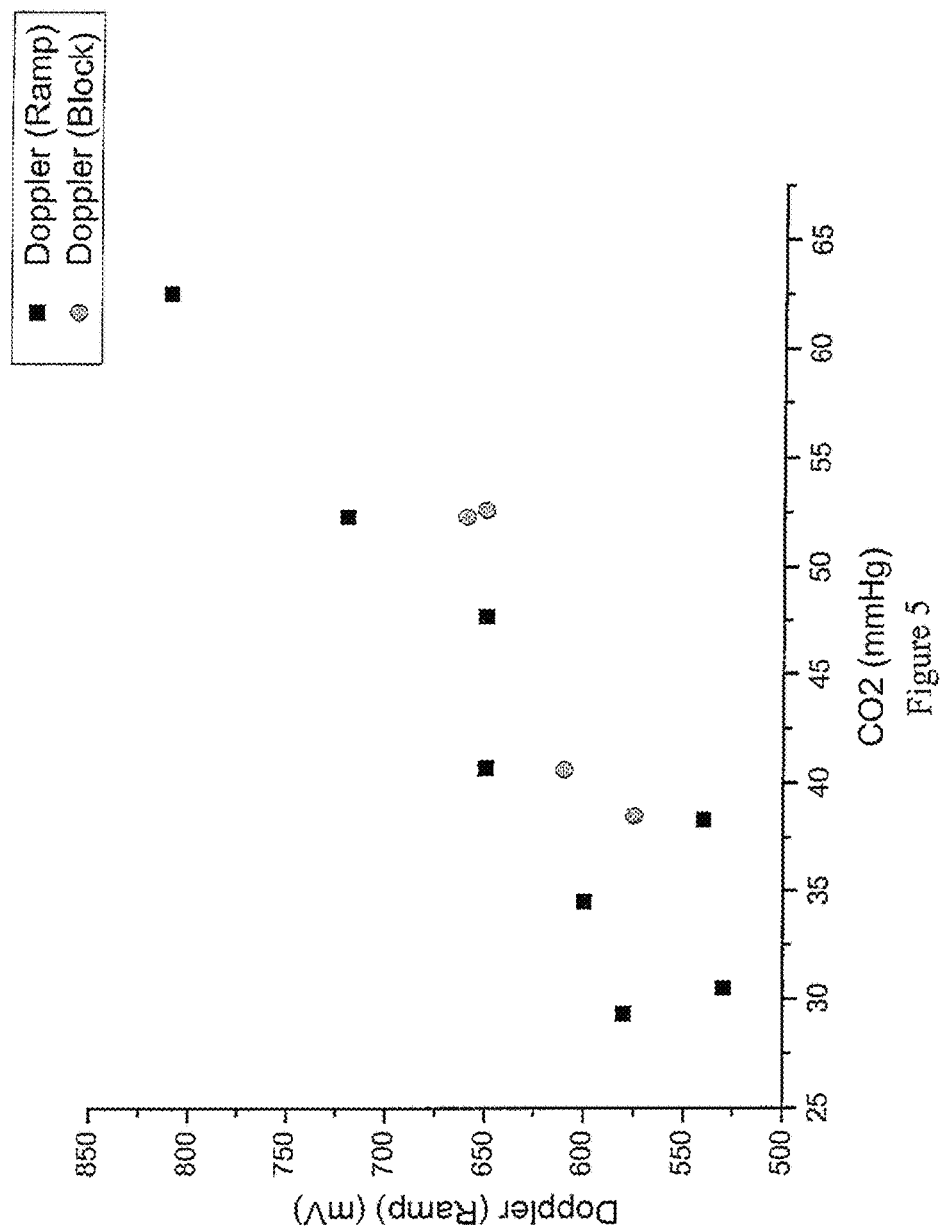
FIG. 5 depicts the Doppler flow through the left anterior descending artery in response to $PaCO_2$ modulation while $PaO_2$ is held constant.

Doppler flow, an ultrasound-based approach which uses sound waves to measure blood flow, was used to show that administration of $CO_2$ leads to vasodilation which results in greater blood flow, while $PaO_2$ is held constant. The Doppler flow was measured in the left anterior descending (LAD) artery. As shown in FIG. 5, as the amount of administered $CO_2$ increases the Doppler flow increases. The relative change in coronary flow velocity was directly proportional to the amount of $CO_2$ administered.

Example 4

Figure 6:
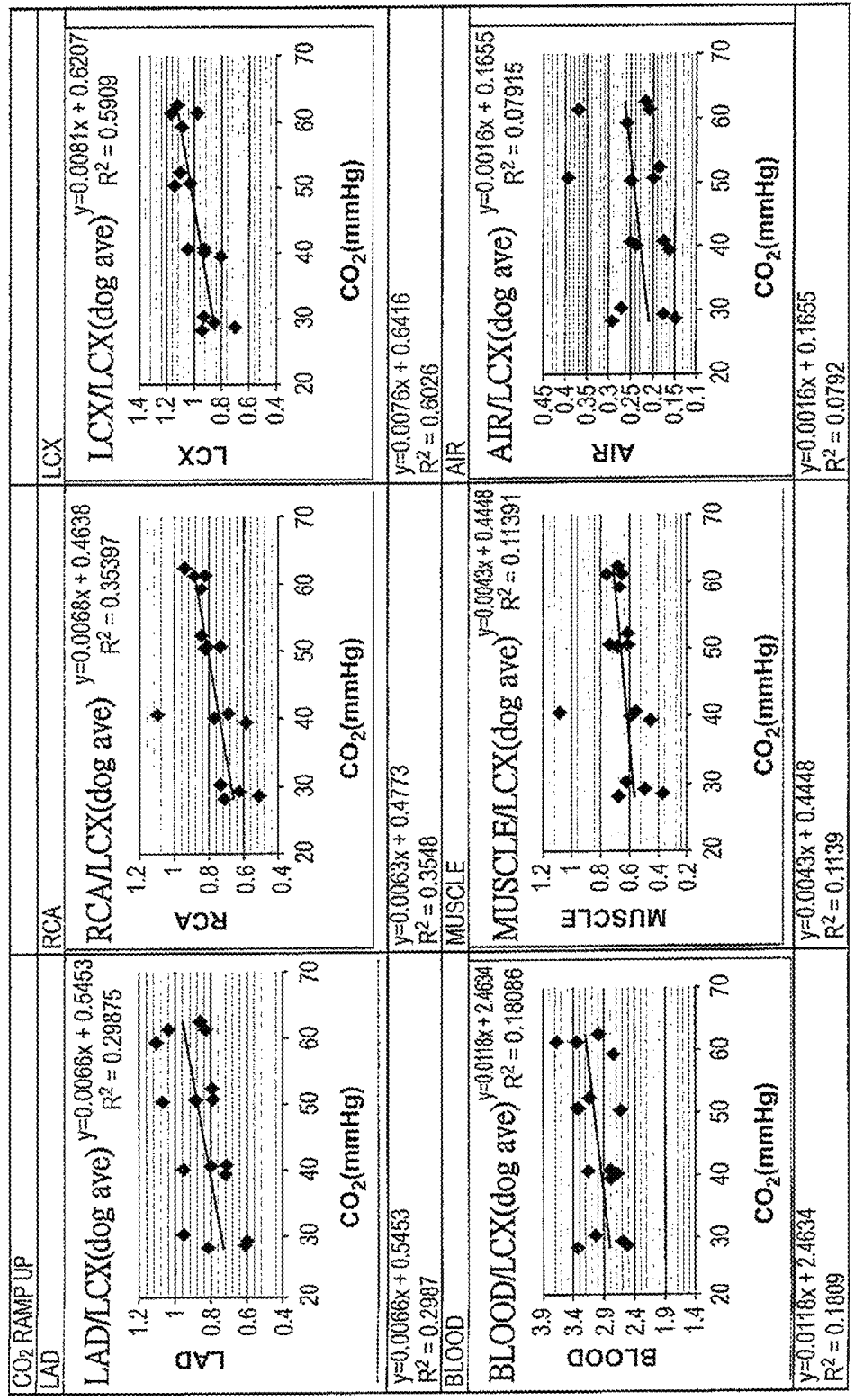
FIG. 6 depicts the Doppler flow through the LAD, RCA and LCX arteries in response to $PaCO_2$ modulation while $PaO_2$ is held constant.
Figure 7:
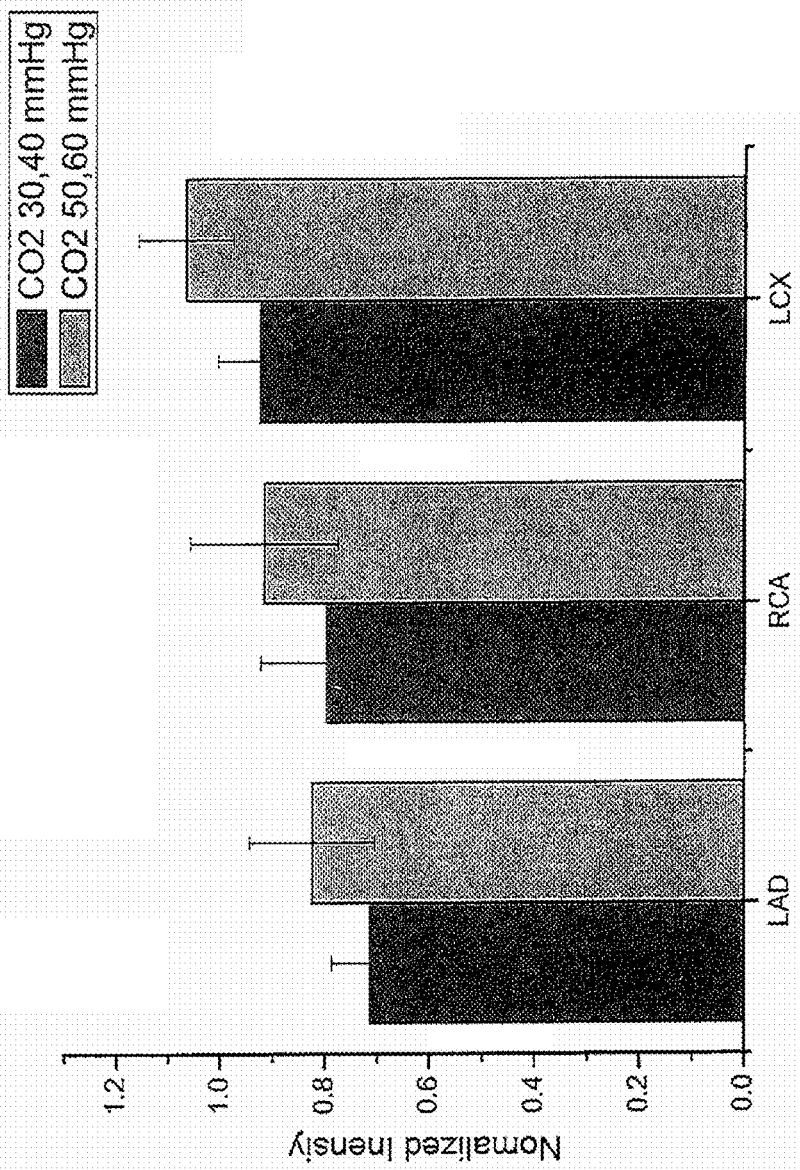
FIG. 7 is a bar graph depicting the territorial myocardial BOLD response to $PaCO_2$ modulations in canines while $PaO_2$ is held constant.
Figure 8:
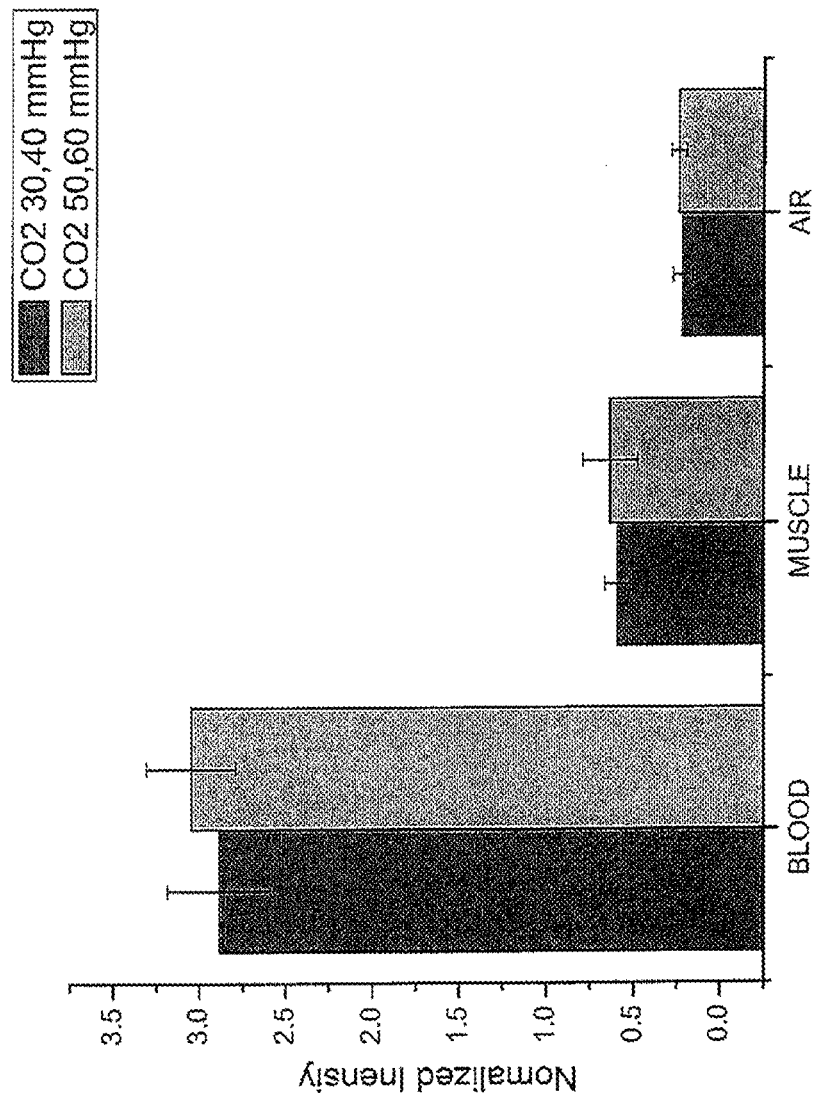
FIG. 8 is a bar graph depicting the BOLD effect associated with $PaCO_2$ modulation in blood, muscle and air while $PaO_2$ is held constant.

Each of the Arteries which Supply Blood to the Myocardium Responds to the $CO_2$ Levels The myocardium is supplied with blood by the left anterior descending (LAD) artery, the right coronary artery (RCA) and the left circumflex (LCX) artery. We measured the blood flow through each of these arteries in response to increasing $CO_2$ supply. As shown in FIG. 6 and summarized in FIG. 7, in each of the three LAD, RCA and LCX arteries, there is a direct correlation between the amount of $CO_2$ administered and the signal intensity; as the amount of administered $CO_2$ increases, the signal intensity, signaling the blood flow, in each of the three arteries increases. Further, as shown in FIG. 6 and summarized in FIG. 8, there was no response to $CO_2$ modulation in control territories such as blood, skeletal muscle or air. As shown in FIG. 9, the mean hyperemic response was approximately 16%.

Example 5

Vascular Reactivity to $CO_2$ Comparable to Adenosine

Figures 10A, 10B:
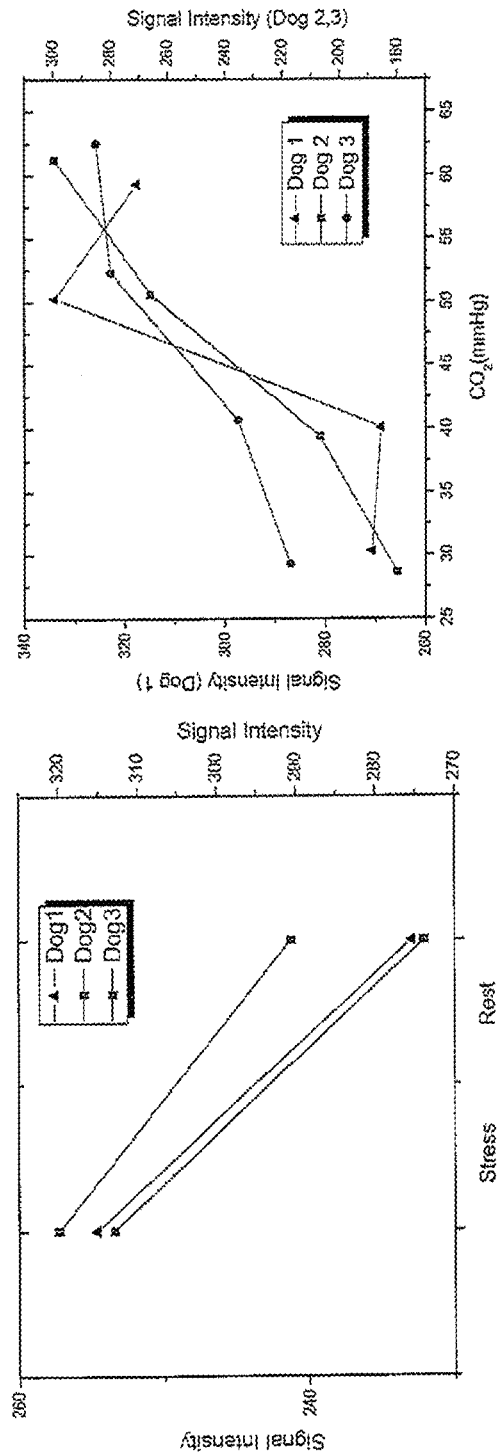
FIG. 10A and FIG. 10B show a comparison of BOLD response to adenosine and $PaCO_2$ (while $PaO_2$ is held constant).

Vascular reactivity of three canines that were administered with adenosine was compared with the vascular reactivity of canines that were administered with $CO_2$. As shown in FIGS. 10A and 10B, the hyperemic adenosine stress BOLD response was approximately 12% compared with 16% in response to $CO_2$.

Figure 11B:
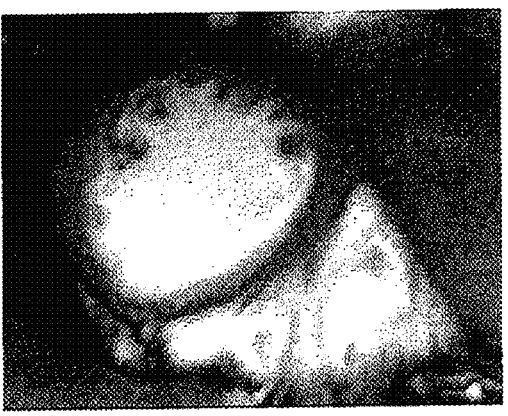
FIG. 11A and FIG. 11B depict the early findings of BOLD response to $PaCO_2$ in humans, while $PaO_2$ is held constant.
Figure 11A:
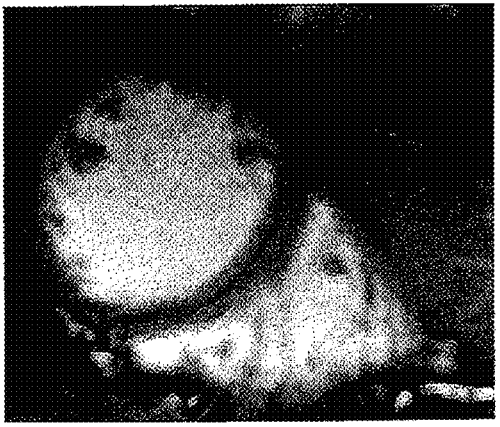

Further, as shown in FIGS. 11A and 11B, early human data shows a hyperemic response of approximately 11% for a partial pressure CO2 (pCO2) change of 10 mmHg, from 35 mmHg to 45 mmHg.

Example 6

Figure 12A:
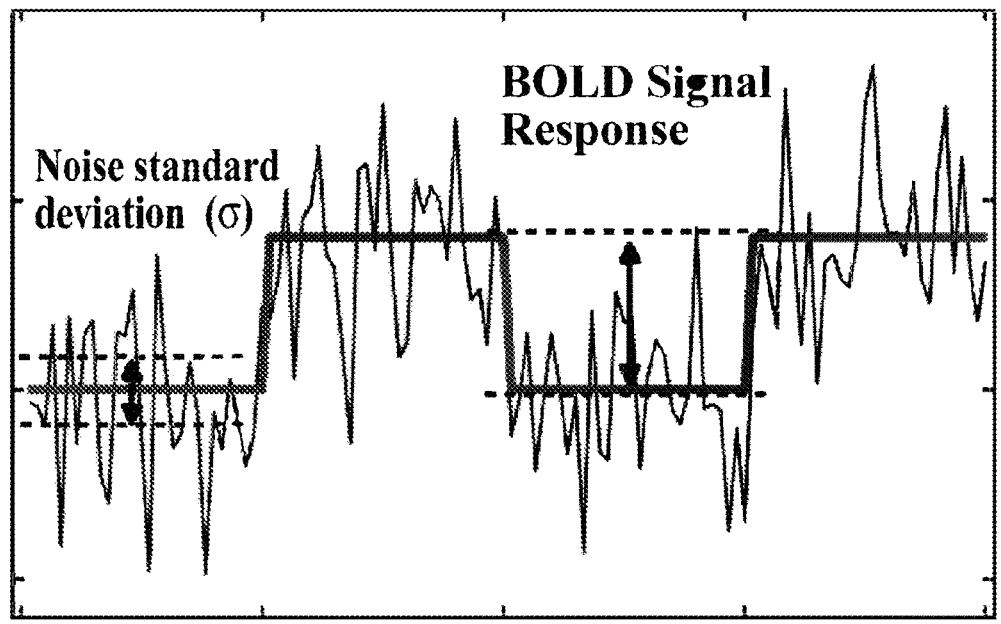
FIG. 12A depicts a simulated BOLD signal for a change in $PaCO_2$ (red line) with definitions for noise variability ($\sigma$=20) and response.
Figure 12B:
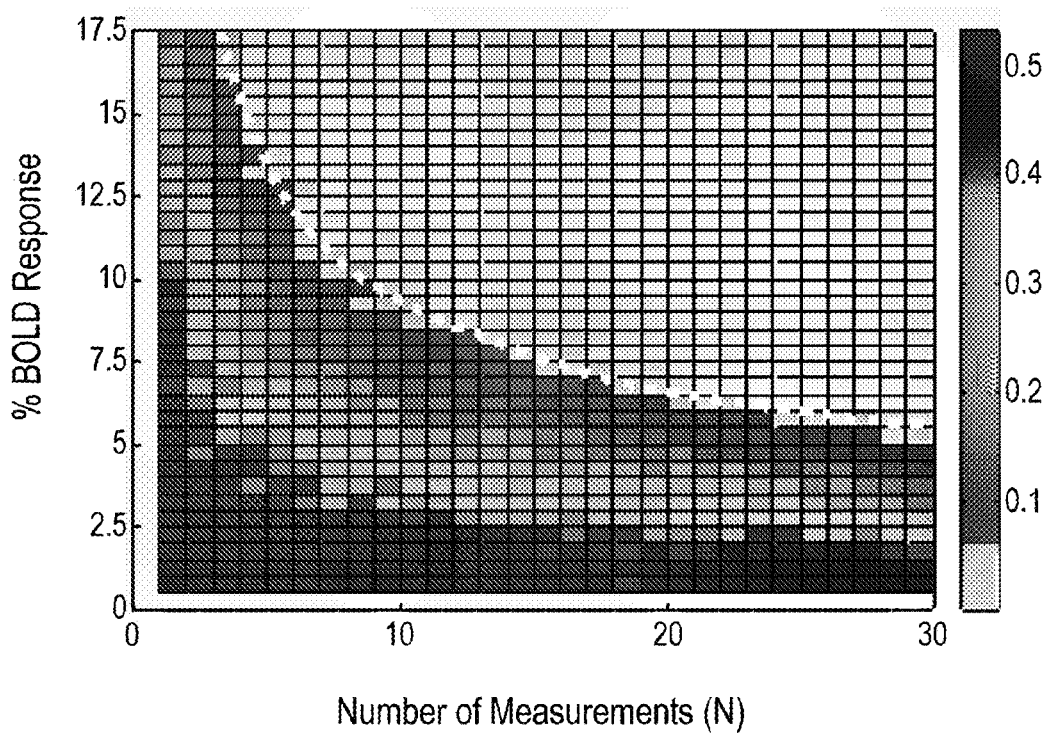
FIG. 12B depicts a relation between BOLD response (y-axis) and the number of measurements (x-axis) required to establish statistical significance (color-coded p-values). For a given BOLD response, the number of repeated measurements (N) required for reliable assessment (p<0.05) of a change from baseline condition lies at the right of the white dotted line. For example, to reliably detect a BOLD response from a voxel with peak BOLD signal response of 10%, greater than 8 measurements are needed. The bar on the right gives the scale for p values associated with the statistical significance.
Figure 14A:
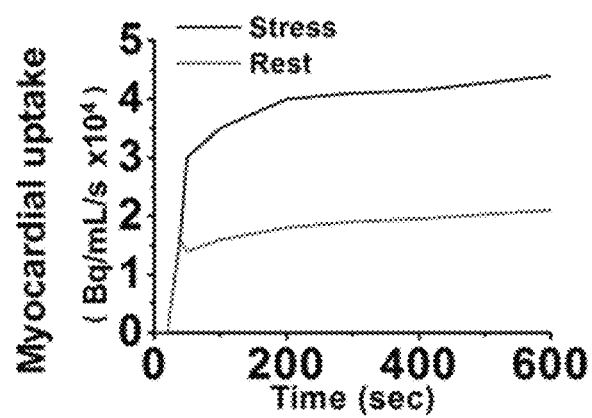
FIGS. 14A-14D depict global and regional myocardial blood flow response to hypercapnia and adenosine in intact canines.
Figure 14B:
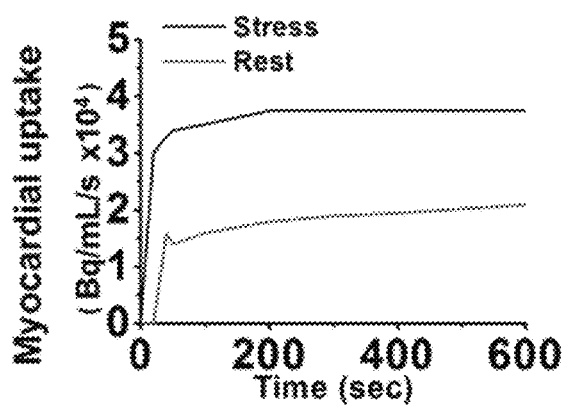
Figure 14C:
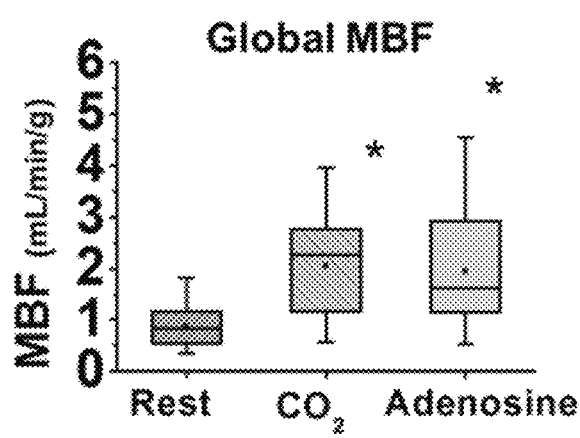
Figure 14D:
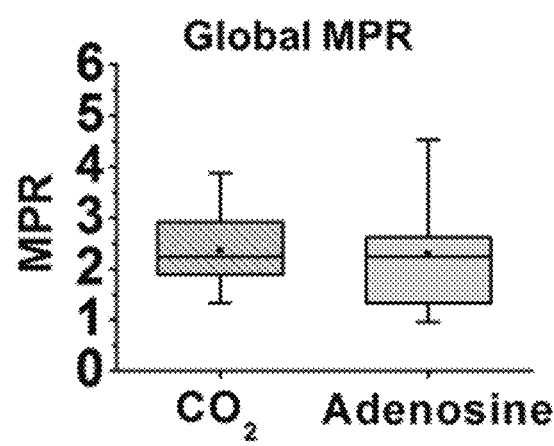

To derive a theoretical understanding of how repeated measurements may affect the BOLD signal response, for a given BOLD response to $PaCO_2$, Applicants performed numerical simulations of statistical fits assuming various peak hyperemic BOLD responses to two different $PaCO_2$ levels (as in FIG. 12A) along with known variability in BOLD signals. The results (FIG. 12B) showed that as the BOLD response decreases, the number of measurements required to establish statistical significance (p<0.05) associated with the BOLD response increases exponentially. This model provides the basis for developing a statistical framework for identifying ischemic volume on the basis of repeated measures.

Example 7

We investigated whether a physiologically tolerable hypercapnic stimulus (~25-mmHg increase in $PaCO_2$) can increase myocardial blood flow (MBF) to that observed with adenosine in three groups of canines: (i) without coronary stenosis; (ii) subjected to non-flow limiting coronary stenosis; and (iii) following pre-administration of caffeine. These studies were conducted by prospectively and independently controlling $PaCO_2$ and combining it with $^{13}$N-ammonia Positron Emission Tomography (PET) measurements, and the extent of effect on MBF due to hypercapnia was compared to adenosine.

The objectives of these studies were twofold: to investigate the effects of PaCO2 on MBF while minimizing contributions from factors that can unintentionally reduce or inaccurately report on sensitivity of PaCO2 on MBF; and to assess whether an independent, precise and rapid establishment of physiologically tolerable level of hypercapnia provides equivalent hyperemia as adenosine, a commonly used pharmacological stimulus for cardiac stress testing with and without pre-administration of caffeine. To address these aims, a clinically relevant animal model was used along with validated strategies for (i) precisely and rapidly establishing desired levels of PaCO2, while holding $PaO_2$ constant; (ii) quantifying MBF in vivo; and (iii) image analysis to derive MBF values across the different coronary supply territories. We compared our findings to the effects of standard dose of adenosine in the same animal models with and without coronary stenosis to quantify MBF and flow deficit regions under peak tolerable PaCO2. To determine whether MBF response to PaCO2 overlaps the same mechanistic path as adenosine, we quantified MBF under hypercapnia and adenosine following caffeine administration. Studies were conducted as described in Yang, H-J et al., J. Nucl. Med. 58: 953-960 (2017), which is hereby incorporated by reference in its entirety.

Prospectively Targeted Hypercapnia as Potent Stimulator of MBF and Its Use for Identifying Regional Impairments in MBF and MPR We found that prospectively targeted hypercapnia was a potent stimulator of MBF. Data are given in FIGS. 13 and 14A-14D. FIG. 13 is a table summarizing the mean arterial $CO_2$, $O_2$ and hemodynamic variables of interest in Group Intact. FIGS. 14A-14D show the mean global MBF and MPR response to hypercapnia in relation to adenosine. Global MBF under adenosine and hypercapnia were both higher than at rest ($p<0.05$, for both) and were not different from one another ($p=0.33$). Global MBF increase under adenosine and hypercapnia were equivalent with a margin of equivalence of 0.26 ml/min/g (⅓ of the SD of the difference in MBF, 0.8 ml/min/g) at $\alpha=0.05$. Global MBF normalized by rate-pressure-product under adenosine ($1.16\times10^{-5}\pm0.80\times10^{-5}$) and hypercapnia ($1.26\times10^{-5}\pm0.56\times10^{-5}$) were significantly different from rest ($0.67\times10^{-5}\pm0.33\times10^{-5}$, $p<0.05$ for both), but were not different from one another ($p=1.00$). Mean global MPR with adenosine and hypercapnia were significantly greater than 2 and were equivalent with a margin of equivalence of 0.50 (⅓ of the SD of the difference in MPR, 1.54) at $\alpha=0.05$. The mean global MPRs did not differ under hypercapnia and adenosine ($p=1.00$). Similar observations were evident for regional MBF and MPR with hypercapnia and adenosine. The observed range of MBF at rest (0.44 to 1.93 ml/min/g) and adenosine (0.47 to 5.10 ml/min/g) and range of MPR under adenosine (1.20 to 4.57) across the animals is consistent with previous reports (Kuhle, W. G. et al., Circulation 86:1004-1017 (1992)). Notably, these results indicate that an increase in MBF is not different from that are observed with adenosine and is not attributable to changes in myocardial oxygen consumption (work) indexed by rate-pressure product.

Figures 15A, 15B:
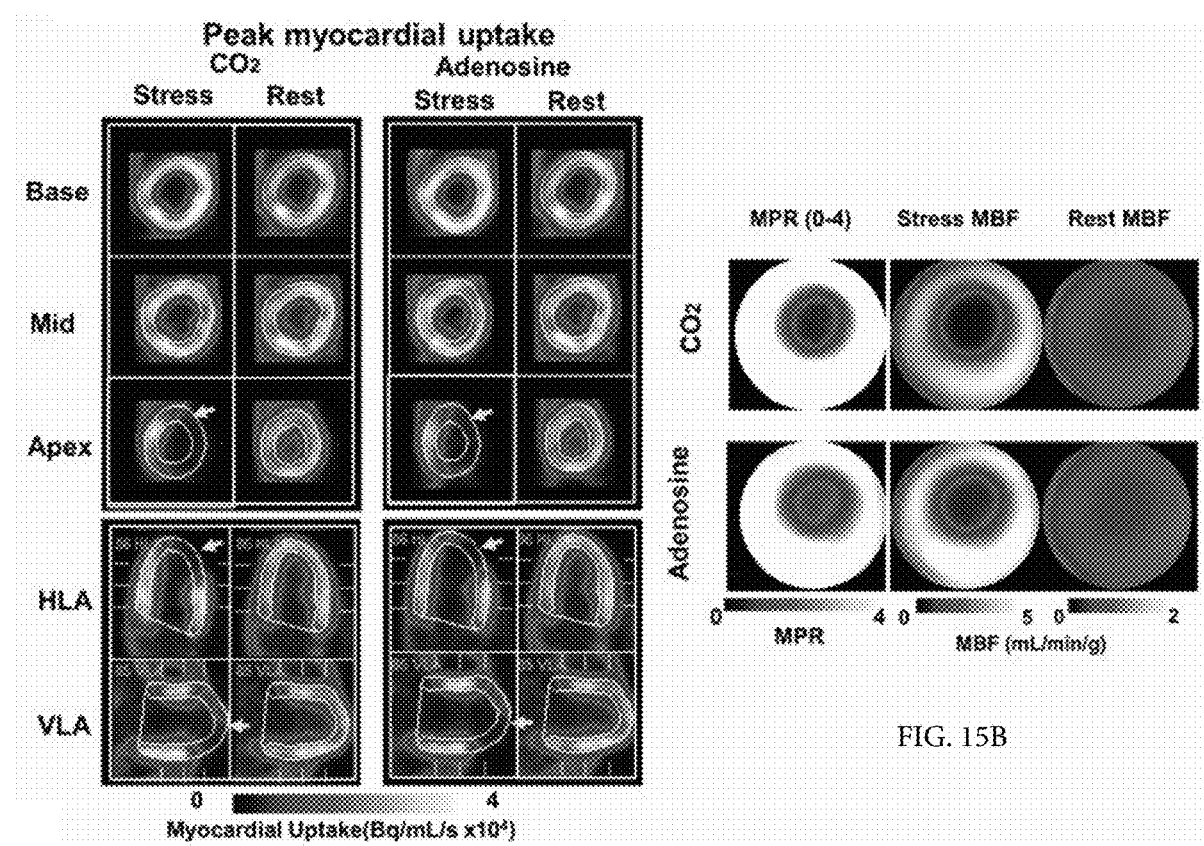
FIGS. 15A-15B depict regional myocardial blood flow response to hypercapnia and adenosine in the presence of coronary stenosis.
Figure 16A:
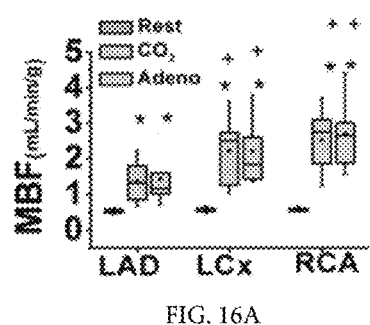
FIGS. 16A-16F depict quantitative measurements of regional myocardial blood flow response to hypercapnia and adenosine in the presence of coronary stenosis.
Figure 16B:
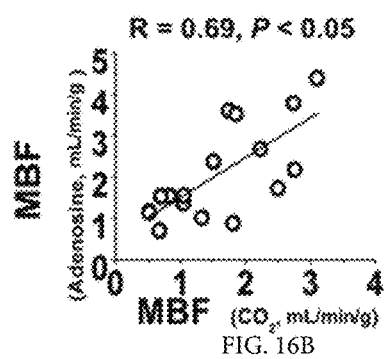
Figure 16E:
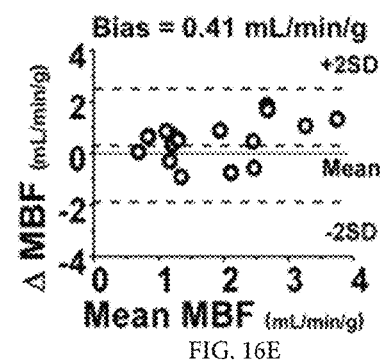
Figure 16C:
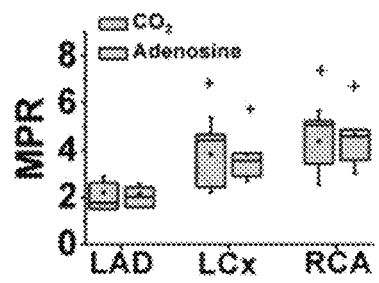
Figure 16D:
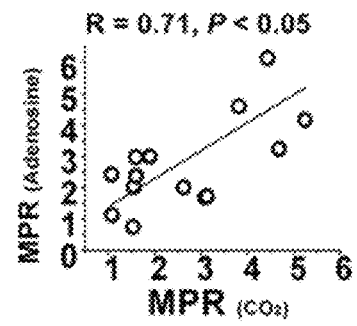
Figure 16F:
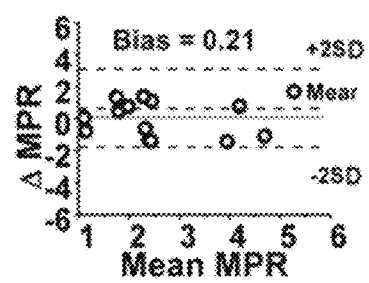

FIGS. 15A and 15B show the mean global and regional MBF and MPR response to hypercapnia in relation to adenosine. FIGS. 16A-16F show the mean regional MBF in LAD, left circumflex artery (LCx) and right coronary artery (RCA) supply territories at rest, hypercapnia and adenosine. MBF values were not different at rest among the different supply territories ($p>0.4$, for all). MBF increased under hypercapnia and adenosine ($p<0.05$, for all territories), albeit the increase in the LAD territory was significantly lower than in the LCx and RCA territories (with hypercapnia and adenosine; both $p<0.05$). MBF under hypercapnia was not different between the LCx and RCA territories (hypercapnia: $p=0.21$); the same was true under adenosine ($p=0.50$). For each myocardial supply territory, MBF under hypercapnia and adenosine were not different ($p=1.00$, for all). Collective comparisons of regional MBF between hypercapnia and adenosine showed significant correlation ($R=0.69$, $p<0.05$) and good agreement (bias=0.41 ml/min/g). MPR values were not higher than 2.0 in LAD territories (hypercapnia: $p=0.48$ and adenosine: $p=0.52$) but were higher than 2.0 in the LCx and RCA ($p<0.05$ for hypercapnia and adenosine) territories. MPR under hypercapnia was not different between the LCx and RCA territories (hypercapnia: $p=0.59$; the same was true under adenosine ($p=0.34$). For each myocardial supply territory, MPR under hypercapnia and adenosine were not different ($p>0.5$ for all). Collective comparisons of regional MPR between hypercapnia and adenosine showed significant correlation ($R=0.71$, $p<0.05$) and good agreement (bias=0.21). Taken together, FIGS. 15A-15B and 16A-16F show that $CO_2$ is able to increase blood flow and the myocardial blood flow reserve to the same extent in healthy and affected territories of the myocardium.

Perfusion Defect Volumes and Visual Scoring Under Hypercapnia Versus Adenosine

Figure 18:
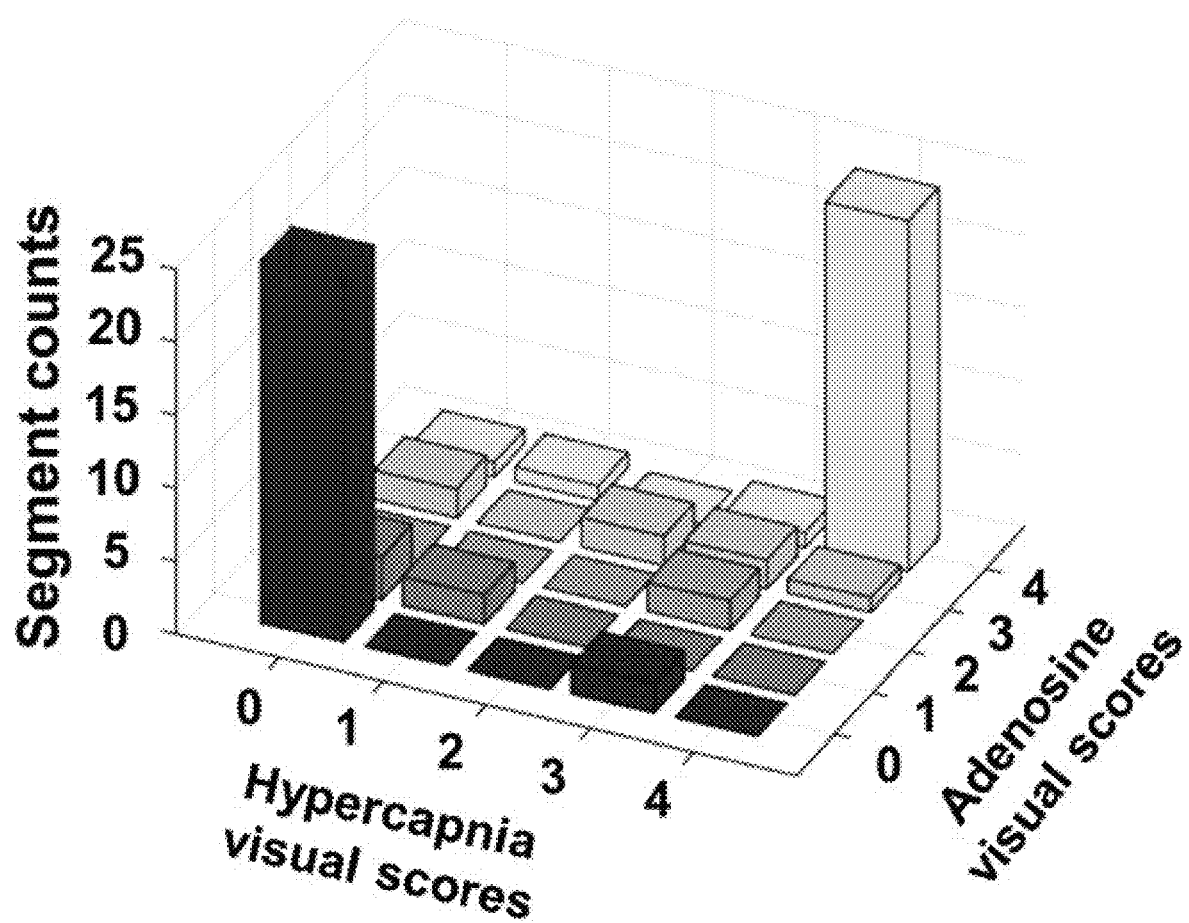
FIG. 18 depicts visual scoring of perfusion defects under hypercapnia and adenosine in the presence of LAD coronary stenosis. Visual scoring (counts) from segments in the stenosis studies are presented in a 3D bar plot. Excellent correspondence in visual scoring between hypercapnia and adenosine is observable (high count rates along the diagonal).
Figure 20A:
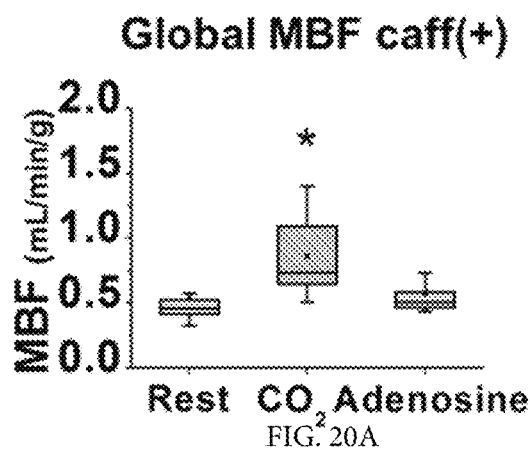
FIGS. 20A-20D depict MBF and MPR response under hypercapnia and adenosine following caffeine administration.
Figure 20B:
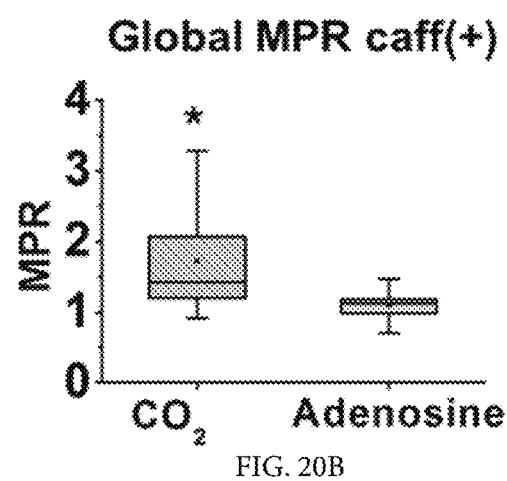
Figure 20C:
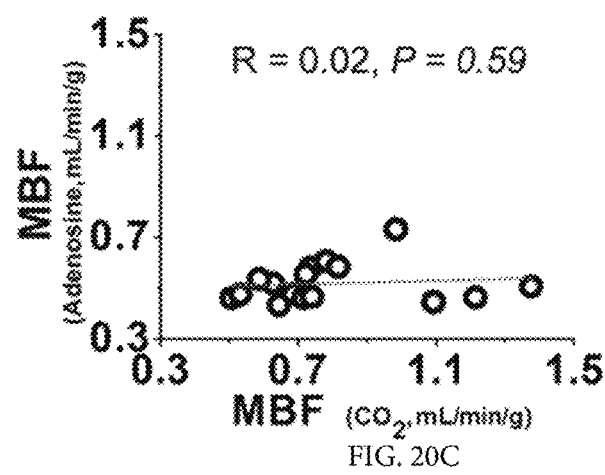
Figure 20D:
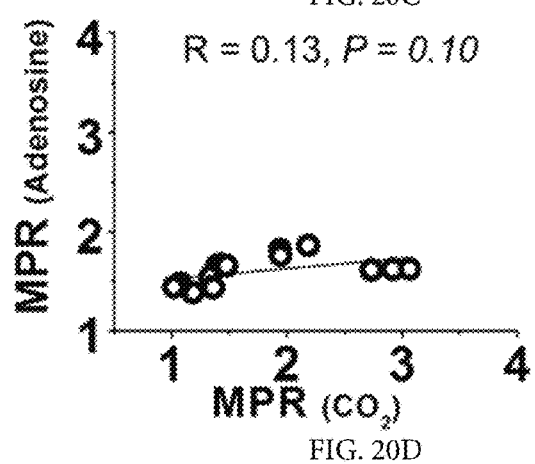

Perfusion defect volumes and visual scoring under hypercapnia vs. adenosine were determined. The total reduction in perfusion volume (TRP, % LV) between stress and rest states is shown in FIGS. 17A-17D. TRP obtained under hypercapnia and adenosine were not different: $25\pm19\%$ (hypercapnia) vs. $27\pm15\%$ (adenosine); $p=0.12$. Direct comparison of TRP within the same subjects under hypercapnia and adenosine were highly correlated ($R=0.85$, $p<0.05$) and were in good agreement (bias=2%). Similar trends were observed from visual scoring analysis. No difference between the scores from hypercapnia and adenosine was observed from a paired sampled Wilcoxon signed rank test ($p=0.26$). Visual scores between hypercapnia and adenosine were concordant with most segments falling onto the diagonal of the scoring matrix (FIG. 18). Hypercapnia also showed high accuracy (0.95), sensitivity (0.89) and specificity (0.98) for detecting affected segments compared to adenosine.

The results in FIGS. 17A-17D and 18 show that the perfusion defect identified with $CO_2$ and adenosine are substantially the same. The perfusion defects identified with $CO_2$ or adenosine were highly correlated ($R=0.85$) with negligible bias (<2%), and an increase of 25 mmHg in arterial $CO_2$ was sufficient to increase blood flow to the levels seen with adenosine. Further, such levels were sufficient for identifying the ischemic territories that emerge from clinically significant coronary narrowing. Moreover, the territories that were identified to have defects using adenosine (i.e., control positives) were accurately captured with $CO_2$ stress as well. The corollary was also true: the regions identified with absolute certainty to have no perfusion defect (i.e., control negatives) were also identified equally accurately with $CO_2$. Thus, this data shows that even visual scoring, which is commonly employed in the clinical setting, can accurately identify the presence of disease on the basis of a 25 mmHg increase in arterial $CO_2$.

Effect of Preadministration of Caffeine on MBF Under Hypercapnia Versus Adenosine Next the effect of pre-administration of caffeine on myocardial blood flow under hypercapnia vs. adenosine was determined. Mean global MBF and MPR following pre- and post-caffeine administration are shown in FIGS. 19 and 20. Results showed that although there is no change in MBF between rest and adenosine, hypercapnia was able to induce myocardial hyperemia. There was a trend towards higher resting MBF prior to caffeine administration but this was not statistically significant ($p=0.09$). However, the resting MBF normalized by rate-pressure-product was significantly higher prior to caffeine ($1.5\times10^{-5}$ (pre-administration) vs $1.0\times10^{-5}$ (post-administration), $p=0.03$). These observations are consistent with reports in humans (Bottcher, M. et al., J. Nucl. Med. 36:2016-2021 (1995)) and are likely related to the influence of caffeine on calcium cycling at rest, which is known to promote vascular smooth muscle contraction. Mean global MBF at rest (post caffeine) and under adenosine were not different ($p=1.00$) and were significantly lower than hypercapnia ($p<0.05$, for both). Under caffeine, there was no correlation between MBF under adenosine and hypercapnia ($R=0.02$, $p=0.59$). Under caffeine, the global MPR under adenosine was lower than under hypercapnia ($p<0.05$). Regional MPR regressed against adenosine and hypercapnia showed a weak and non-significant correlation (R=0.13, p=0.10). These findings of differential MBF response to hypercapnia and adenosine following pre-administration of caffeine suggest that the mechanism of action mediating myocardial hyperemia by these stimuli are at least partly different. These data also show that carbon dioxide can produce the requisite hyperemic response for assessing ischemic territories despite consumption of caffeine, in contrast to some hyperemia-inducing drugs which do not produce reliable assessments in subjects who have consumed caffeine beforehand.

In sum, these results show that in the absence of stenosis, mean MBF under hypercapnia was 2.1±0.9 ml/min/g and adenosine was 2.2±1.1 ml/min/g were significantly higher than at rest (0.9±0.5 ml/min/g, P<0.05); and were not different from each other (P=0.30). Under left-anterior descending coronary (LAD) stenosis, MBF increased in response to hypercapnia and adenosine (p<0.05, all territories) but the effect was significantly lower than in the LAD territory (with hypercapnia and adenosine; both p<0.05). Mean perfusion defect volumes measured with adenosine and hypercapnia were significantly correlated (R=0.85) and were not different (p=0.12). Following pre-administration of caffeine, a known inhibitor of adenosine, resting MBF decreased and hypercapnia increased MBF but not adenosine (p<0.05). The results indicate that arterial blood $CO_2$ tension when increased by 25 mmHg can induce MBF to the same level as a standard dose of adenosine.

The results thus demonstrate substantial similarity in physiologic outcomes on several scores between a clinically-relevant hyperemia-inducing drug (adenosine) and carbon dioxide. It is noted that, in addition to having significant negative side effects, adenosine's negative effects can last for hours whereas carbon dioxide can be exhaled off in a few breaths. Importantly, it is not only the hyperemia inducing effect on the heart as a whole that is comparable for carbon dioxide and adenosine; the identified blood flow deficit is also the same (for both location and relative volume of deficit, which influences treatment choices in the clinic).

There was also excellent concordance in how blind observers (blind to whether adenosine or $CO_2$ was used to cause the effect) scored the images in terms of deficit severity. Thus, $CO_2$ is able to discriminate ischemic heart disease in a clinically relevant setting, indicating that prospectively targeted arterial $CO_2$ can be used as an alternative to current pharmacological vasodilators for cardiac stress testing.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method of inducing hyperemia to diagnose coronary heart disease in a subject in need thereof, comprising:
   administering a carbon dioxide ($CO_2$)-containing gas to the subject;
   attaining at least one increase in the subject's coronary arterial partial pressure of carbon dioxide ($PaCO_2$) sufficient for diagnosing coronary heart disease from imaging data; and
   imaging the heart during a period in which the at least one increase in $PaCO_2$ is measurable, to produce imaging data indicative of a cardiovascular-disease-associated vasoreactive response in at least one coronary blood vessel or region of the heart,
   wherein the at least one increase in the $PaCO_2$ is sufficient for inducing a vasoreactive response with a myocardial blood flow during the increased $PaCO_2$ that is about 2.3 times, or more than 2 times, as high as a myocardial blood flow before the at least one increase in $PaCO_2$.

2. The method of claim 1 comprising attaining the at least one increase in $PaCO_2$ in a block manner.

3. The method of claim 1, comprising administering $CO_2$ via inhalation to attain a predetermined $PaCO_2$.

4. The method of claim 1, wherein the cardiovascular disease-associated vasoreactive response is a compromised increase in blood flow.

5. The method of claim 1, wherein the imaging method is positron emission tomography (PET) or single photon emission computed tomography (SPECT) and the measure of the cardiovascular-disease-associated vasoreactive response is the presence or absence of a threshold increase in blood flow.

6. The method of claim 1, wherein the imaging data is indicative of the presence or absence of a two-fold increase in blood flow.

7. The method of claim 1, wherein the $PaCO_2$ is increased and decreased in a block manner repeatedly.

8. The method of claim 1, wherein the imaging data are obtained by magnetic resonance imaging (MRI).

9. The method of claim 1, wherein the imaging data are a change in signal intensity of a blood oxygen level dependent (BOLD) MRI signal.

10. The method of claim 8, further comprising:
    (i) registering and segmenting MRI images to obtain the myocardial dynamic volume, and
    (ii) identifying ischemic territory and quantifying image volume.

11. The method of claim 9, further comprising:
    (i) imaging the myocardium to obtain free-breathing cardiac phase resolved 3D myocardial BOLD images;

(ii) registering and segmenting the images to obtain the myocardial dynamic volume; and (iii) identifying ischemic territory and quantifying image volume.

12. The method of claim 1, wherein the administration of the $CO_2$-containing gas increases the $PaCO_2$ in the subject by about 22 to about 28 mm Hg.

13. The method of claim 12, wherein the administration of the $CO_2$-containing gas increases the $PaCO_2$ in the subject by about 25 mm Hg.

14. The method of claim 1, wherein the coronary $PaCO_2$ is in a range between 20 mm Hg and 65 mmHg.

15. A method for imaging hyperemia in a subject in need of a diagnostic assessment of cardiovascular disease comprising administering a carbon dioxide ($CO_2$) containing gas in a non-therapeutic diagnostic setting, attaining at least one selected increase in a subject's coronary arterial partial pressure of carbon dioxide ($PaCO_2$) sufficient for diagnosing coronary heart disease from imaging data and imaging the heart during a period in which the selected increase in $PaCO_2$ is measurable, wherein the imaging data is selected to be indicative of a cardiovascular-disease-associated vasoreactive response in at least one coronary blood vessel or region of the heart, and wherein the at least one selected increase in the $PaCO_2$ is sufficient for inducing a vasoreactive response with a myocardial blood flow during the increased $PaCO_2$ that is about 2.3 times, or more than 2 times, as high as a myocardial blood flow before the at least one increase in $PaCO_2$.

16. The method of claim 15, wherein the cardiovascular-disease associated vasoreactive response is comparable to a vasodilatory response produced by administering a hyperemia inducing drug for a duration and in amount per unit of time effective to assess coronary disease.

17. A method for controlling a gas flow controller during a cardiac imaging procedure, the gas flow controller operable to deliver controlled amounts of carbon dioxide for inspiration by a subject during free breathing, the method comprising operating the gas mass flow controller to administer controlled amounts of carbon dioxide to attain an at least one altered level of carbon dioxide in the subject's arterial blood, the at least one altered level of carbon dioxide selected to induce a selected hyperemic response in the subject's myocardium over a time period selected for imaging the selected hyperemic response, the selected hyperemic response predetermined to enable at least one segment of the subject's myocardium with a reduced hyperemic response to be identified in the cardiac imaging procedure, wherein the selected hyperemic response results in a myocardial blood flow during the altered level of carbon dioxide that is about 2.3 times, or more than 2 times, as high as a myocardial blood flow before the altered level of carbon dioxide.

18. The method of claim 17, wherein the reduced hyperemic response is a decrease in a ratio of myocardial perfusion at stress to myocardial perfusion at rest to 2:1.

19. The method of claim 17, wherein the selected hyperemic response is induced by attaining a carbon dioxide level of 60 to 65 mm of Hg for at least one to two minutes.

20. The method of claim 17, wherein the altered level of carbon dioxide is a 25 mm of Hg increase from a previous level, optionally a measured baseline level for the subject, optionally a baseline level for the subject at rest, optionally a baseline level for the subject when the subject is breathing at a regulated elevated minute volume.

* * * * *